United States Patent [19]

Ahnell et al.

[11] Patent Number: 4,971,900
[45] Date of Patent: Nov. 20, 1990

[54] METHOD FOR THE DETECTION OF BIOLOGICALLY ACTIVE AGENTS

[75] Inventors: Joseph E. Ahnell, Hydes; H. Mark Perks; Mark L. Sussman, both of Baltimore; Gregory Tice, Lutherville, all of Md.

[73] Assignee: Becton, Dickinson and Company, Franklin Lakes, N.J.

[21] Appl. No.: 171,499

[22] Filed: Mar. 21, 1988

Related U.S. Application Data

[63] Continuation of Ser. No. 597,633, Apr. 6, 1984.

[51] Int. Cl.$^5$ .......................... C12Q 1/04; C12M 1/04
[52] U.S. Cl. ........................................ 435/29; 435/34; 435/291; 435/313; 435/807; 436/146
[58] Field of Search .................. 435/29, 34, 35, 38, 435/39, 40, 291, 299, 313, 807; 422/68; 436/146

[56] References Cited

U.S. PATENT DOCUMENTS

| | | | |
|---|---|---|---|
| 4,073,691 | 2/1978 | Ahnell et al. | 435/34 |
| 4,182,656 | 1/1980 | Ahnell et al. | 435/34 |
| 4,220,858 | 9/1980 | Ikeguchi et al. | 422/68 X |

FOREIGN PATENT DOCUMENTS 2062005  5/1981  United Kingdom .................. 435/34

Primary Examiner—Robert A. Wax
Assistant Examiner—J. D. Waack
Attorney, Agent, or Firm—James McBride; Robert P. Grindle; Aaron Passman

[57] ABSTRACT

An apparatus and method for the detection of the growth of microorganisms through infrared analysis of a sample of the gas produced by growth of the microorganism is descirbed. In the method, a sample of the headspace gas in a vial containing a growth medium which has been inoculated with a sample suspected of containing a microorganism is removed and transferred to a sample cell where infrared analysis is used to determine the presence of carbon dioxide, if any, produced by the growth of the microorganism.

8 Claims, 29 Drawing Sheets

METHOD FOR THE DETECTION OF BIOLOGICALLY ACTIVE AGENTS

This is a continuation of application Ser. No. 597,633, filed Apr. 6, 1984.

BACKGROUND OF THE INVENTION

1. Field of the Invention

The present invention relates generally to a method and apparatus for detecting biological activity. More particularly, the present invention relates to a method for making rapid analysis of materials in which the presence of microorganisms or the like is suspected by infrared analysis of a sample of the head space gas of a container in a sample cell located externally from the container.

When, for example, bacteria are cultured in a suitable medium including a carbon source, such as glucose, the carbon source is broken down to form $CO_2$ during the growth and metabolism of the bacteria. It would be desirable to provide a rapid, sensitive method for the analysis of the gaseous atmosphere produced over the growth medium in the head space in order to determine the presence or absence of biological activity.

2. Description of the Prior Art

In many fields of endeavor it is important to be able to determine whether or not substances are contaminated with biologically active agents such as bacteria and the like. Examples of such fields are the medical field, the food processing industry, the pharmaceutical industry, the cosmetics industry and the field of public health It has long been a standard practice to place a sample of material to be tested for the presence of biologically active agents on a semisolid nutrient medium contained in a Petri dish and to make visual observations of the resulting microbial growth, if any. A similar procedure involves the inoculation of a sterile vial or bottle of liquid nutrient medium with the suspect material, again followed by visual detection of growth. Not only are such methods slow and laborious, but because they depend upon the subjective judgment of individual human observers, the result obtained is not uniformly reliable.

Techniques have also been developed for the detection of bacteria which involve the incubation of a sample of material to be tested in a closed container with a radioactive isotope labeled culture medium with subsequent monitoring of the atmosphere in the container above the medium to determine whether or not radioactive gases are produced. A system of this type is disclosed in U.S. Pat. Nos. 3,676,679 and 3,935,073. Such systems are rapid and reliable, but they suffer from a number of disadvantages resulting primarily from the use of radioactive materials. Radioisotope labeled materials are expensive and require special handling during storage, use and disposal. Moreover, although the levels of radioactivity encountered in using such systems are very low, prospective users may be deterred by personal fears of radioactivity.

Systems have been described which do not require the use of radioactivity in any manner. U.S. Pat. No. 4,182,656 describes a method for the detection of biologically active agents based upon utilization of substrates enriched with stable Carbon-13. Although this method eliminates any requirement for radioisotopes in the detection system, nutrients enriched with Carbon-13 are less available and considerably more expensive than their radiolabled counterparts. Because $^{13}CO_2$ has molecular properties very nearly the same as $^{12}CO_2$, the most prevalent isotopic form of carbon dioxide, and because $^{13}C$ comprises better than 1% of all carbon in the environment, special care must be taken to insure that $^{13}C$ carbon dioxide is detected preferentially while ambient carbon dioxide is ignored. A mass spectrometer is generally used to detect changes in the relative abundance of stable isotopes, and was used in the development of the forementioned patent. Mass spectrometry requires relatively sophisticated high-vacuum instrumentation, and is thus not a suitable detection means for application in the typical microbiology laboratory.

U.S. Pat. No. 4,073,691 discloses a non-radiometric means for detection of biologically active agents through detection of any change in the character of the gas present over a liquid growth medium contained in a sealed vial system. Changes in the character of the gas are determined by measurement of the ratio of the selected product gas to an inert reference gas also present in the vial measurements made before and after the vial has been subjected to conditions conducive to bacterial growth. The inclusion of an inert reference gas for ratio measurement purposes requires that the detection system be responsive to $CO_2$ liberated as a consequence of metabolism as well as to the inert reference gas, complicating the instrumentation required for such measurement. The concentration of the inert gas present in the culture gas used with such a system must be known and reproducible from lot to lot of culture gas, further complicating the overall detection system.

The use of radioisotopes or stable isotopes, or the use of inert reference materials has generally been considered necessary in order to provide for the detection of small quantities of gases produced by metabolism. Of the various gases produced by bacterial metabolism, carbon dioxide is the gas most commonly generated by the various families of bacteria, yeasts, and other primitive organisms. There thus exists a need for an instrumental system for measuring metabolically- produced carbon dioxide to detect bacteria and the like which does not require isotopic enrichment or labeling of nutrients and does not depend upon addition of any reference inert gas to the culture vial.

It is thus an object of the present invention to provide a rapid method for detecting the presence or absence of biologically active agents.

Another object of the invention is to provide a method of detecting the presence or absence of biologically active agents which uses comparatively inexpensive materials in conjunction with relatively straightforward instrumentation.

A further object of the invention is to provide an instrumental method for detecting the presence or absence of biologically active agents which is not subject to subjective interpretation.

An additional object of the present invention is to provide an instrumental system for detecting the presence or absence of biological activity which avoids the use of isotopically enriched or labeled nutrients, or the addition of inert material used as a reference for concentration ratio measurement.

It is yet a further object of the invention to provide an instrument system utilizing infrared analysis for the detection of biologically active agents which provides optimum detection sensitivity through matching of the head space carbon dioxide content of manufactured culture containers with the external culture gas supplied to the instrument for testing, calibration and purging purposes.

SUMMARY OF THE INVENTION

These and other objects of the invention are achieved by providing a method for detecting the presence of biologically active agents comprising the following steps:

A sealable sterile container, usually referred to herein as a "vial", is provided containing a sterile, non-isotopic culture medium. The medium contains a controlled concentration of dissolved carbon dioxide. The head space gas above the medium contains carbon dioxide in equilibrium with the culture medium. The concentration of carbon dioxide in the container head space and the concentration of carbon dioxide in the bottled gas provided for use with instrumental testing are substantially equal at a given medium pH and at the desired incubation temperature. The bottled gas provided for the various instrumental testing functions is referred to herein as "culture gas".

A sample of material to be tested for biological activity is introduced into the container and the container is sealed. The container is then subjected to conditions conducive to the occurrence of normal metabolic processes for a period of time sufficient to cause production of gaseous carbon dioxide by metabolism of various carbon sources in the medium if bacteria are present in the introduced sample.

The vial head space gas is then withdrawn from the vial, circulated through the sample chamber of an infrared detection system to determine the concentration of carbon dioxide in the container head space. Any significant increase in the concentration of $CO_2$ in the container head space gas above the concentration of $CO_2$ present in the bottled culture gas is evidence of biological activity. While not so limited, the method of the invention is particularly applicable to the detection of medically significant bacteria.

If the sample to be tested produces a background level of metabolic activity, such as the metabolic activity of fresh whole blood, the culture gas may be matched in $CO_2$ concentration to the vial head space gas achieved at the desired incubation temperature once the sample of blood or other material has been added. The presence int he sample of bacteria, yeasts, or the like will then be detected as an increase in the vial head space $CO_2$ concentration above this normal level, the latter being matched by the $CO_2$ concentration of the culture gas.

The invention also includes apparatus to perform the method described. The apparatus includes a container adapted to receive a sample of material to be analyzed for biological activity together with a growth medium which includes various carbon sources capable of supporting normal metabolic processes, one result of which is the production of carbon dioxide. Also provided are mans to sample the head space gas of said container. Also provided is means to measure the concentration of $CO_2$ present in a quantity of the gas via infrared analysis. The sampling means and the measurement means are intercommunicated by means of a pneumatic system. Pumping means are provided to circulate head space gas from the container through the $CO_2$ detection system and back to the container. Means to purge the gas handling system with bottled culture gas to remove any vestige of sample gas from the circulation and measurement systems and means to test the gas handling system to insure proper operation of the circulating pump, proper pressure of the culture gas supply, proper pneumatic conductance of the container gas sampling means, proper operation of the infrared detection system, and proper $CO_2$ content of the culture gas are also provided.

The apparatus preferably provides means to rapidly and sequentially analyze a plurality of test containers, each containing an individual sample of material to be tested for biological activity. In one preferred form of the apparatus containers are firmly held in a rectangular array by means of a tray designed for the purpose. Means are provided to translate the head space gas sampling assembly over a row of containers along one dimension of the array. Additional means are provided to translate the tray along the dimension of the array perpendicular to the first so as to provide the gas sampling means access to each column of the tray. Container analysis is carried out sequentially for all vials in a row of a given column, followed by tray translation to present tne next column for testing.

Apparatus control and data processing means are provided via a microprocessor-based system with program storage in read-only memory (ROM) and data storage in random access memory (RAM). Operator interface is provided by a standard computer terminal connected to the system using the RS-232C serial communications protocol. A similar RS-232C port is provided to communicate with an external data system.

Instrument software provides the user with means to set instrument operating parameters, set detection criteria upon which to base positive results, log specimen containers onto the system, obtain a history of results for specimens under test, obtain a listing of new positive results, conduct a manual test of specimen containers exclusive of the automatic protocol, and conduct daily user maintenance of the system.

In each of FIGS. 7-12 the plot defined by the solid line represents the average of 9 or 10 inoculated samples while the plot defined by the dotted line represents the average of 40 uninoculated blood control samples.

Figure 7:
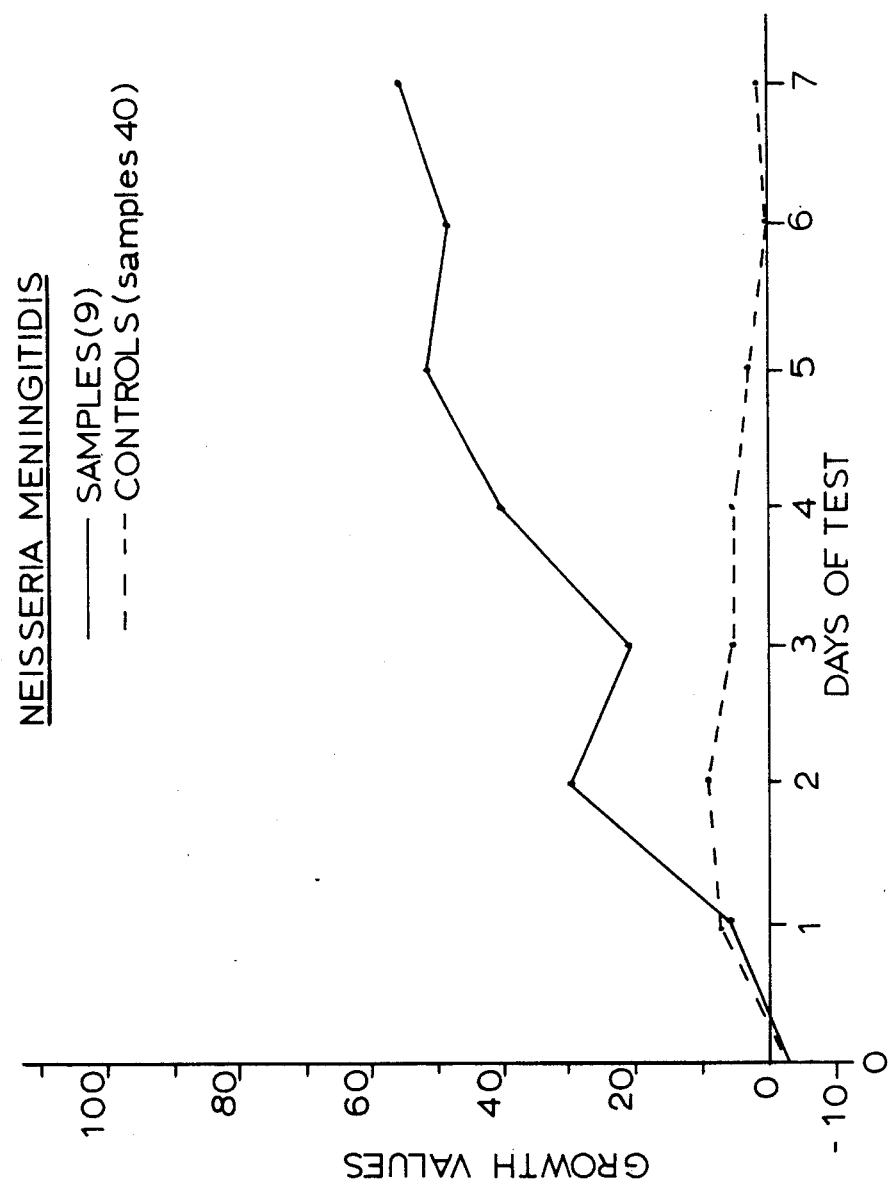

FIG. 7 is a graph depicting results of an infrared detection study conducted with the fastidious microorganism *Neisseria meningitidis* tested aerobically.

Figure 8:
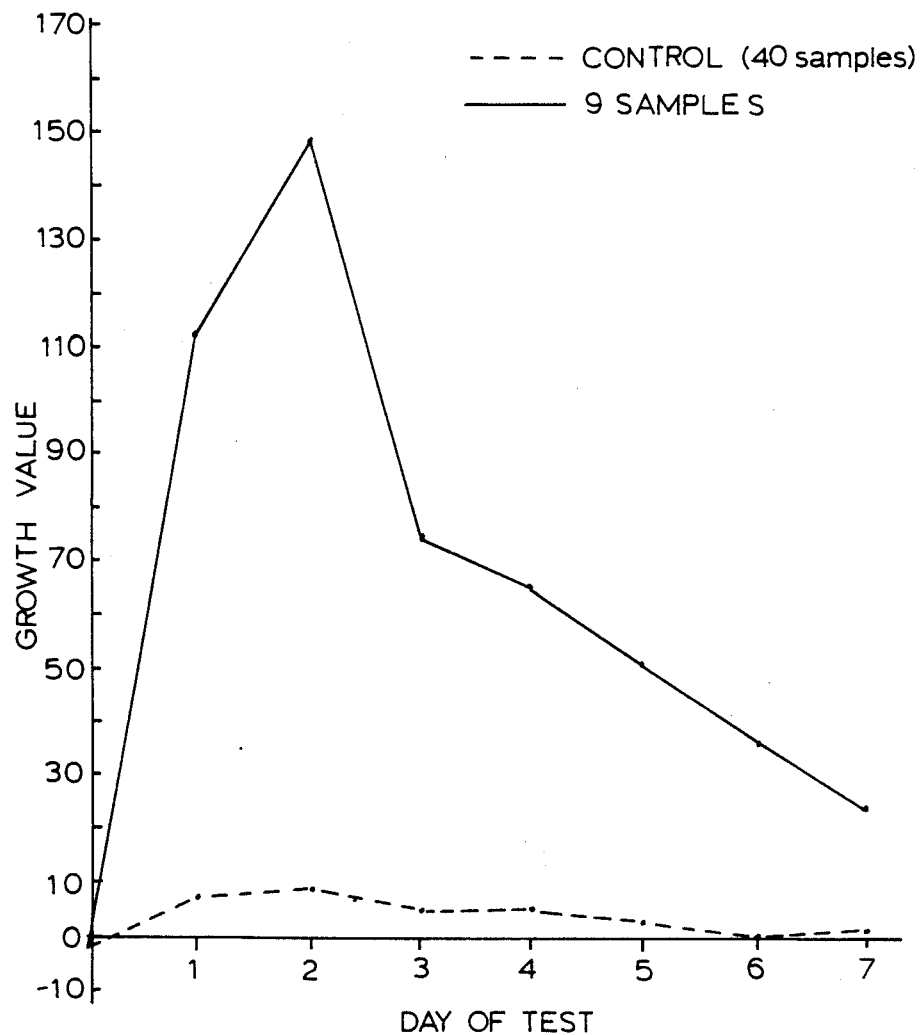

FIG. 8 is a graph depicting results of an infrared detection study conducted with the fastidious microorganism *Streptococcus pneumoniae* tested aerobically.

Figure 9:
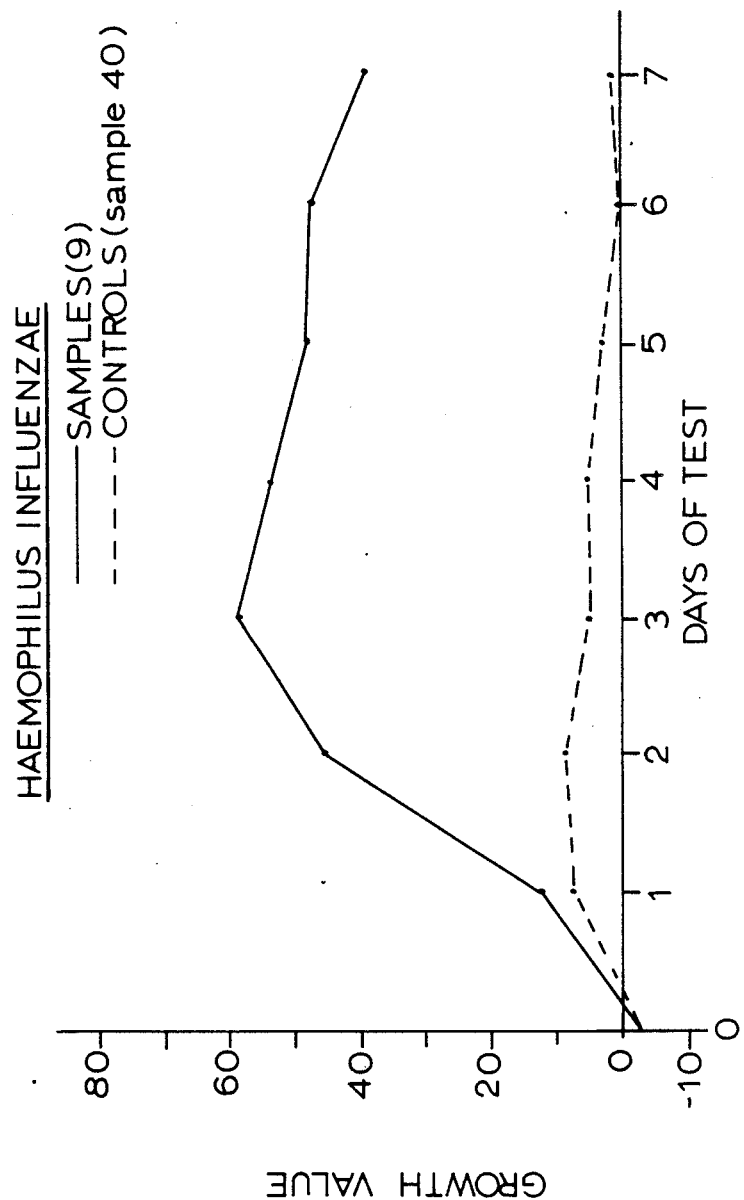

FIG. 9 is a graph depicting results of an infrared detection study conducted with the fastidious microorganism *Haemophilus influenzae* tested aerobically.

Figure 10:
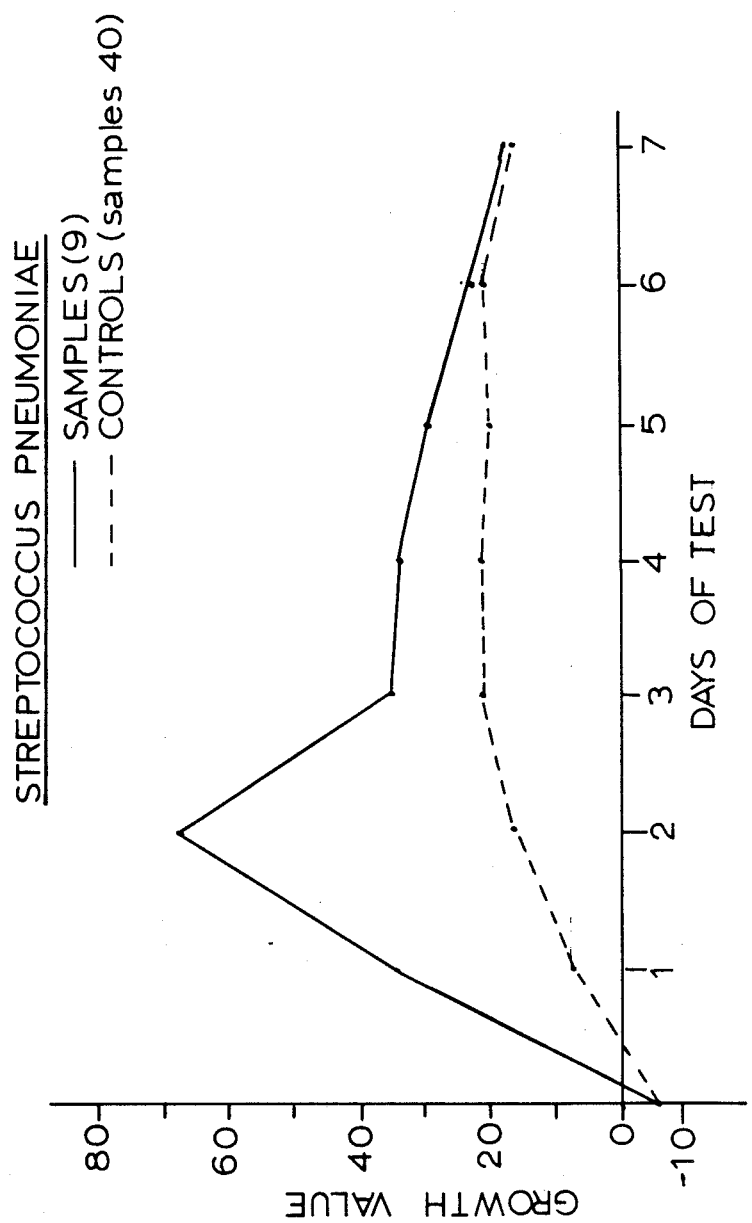

FIG. 10 is a graph depicting results of an infrared detection study conducted with the fastidious microorganism *Streptococcus pneumoniae* tested anaerobically.

Figure 11:
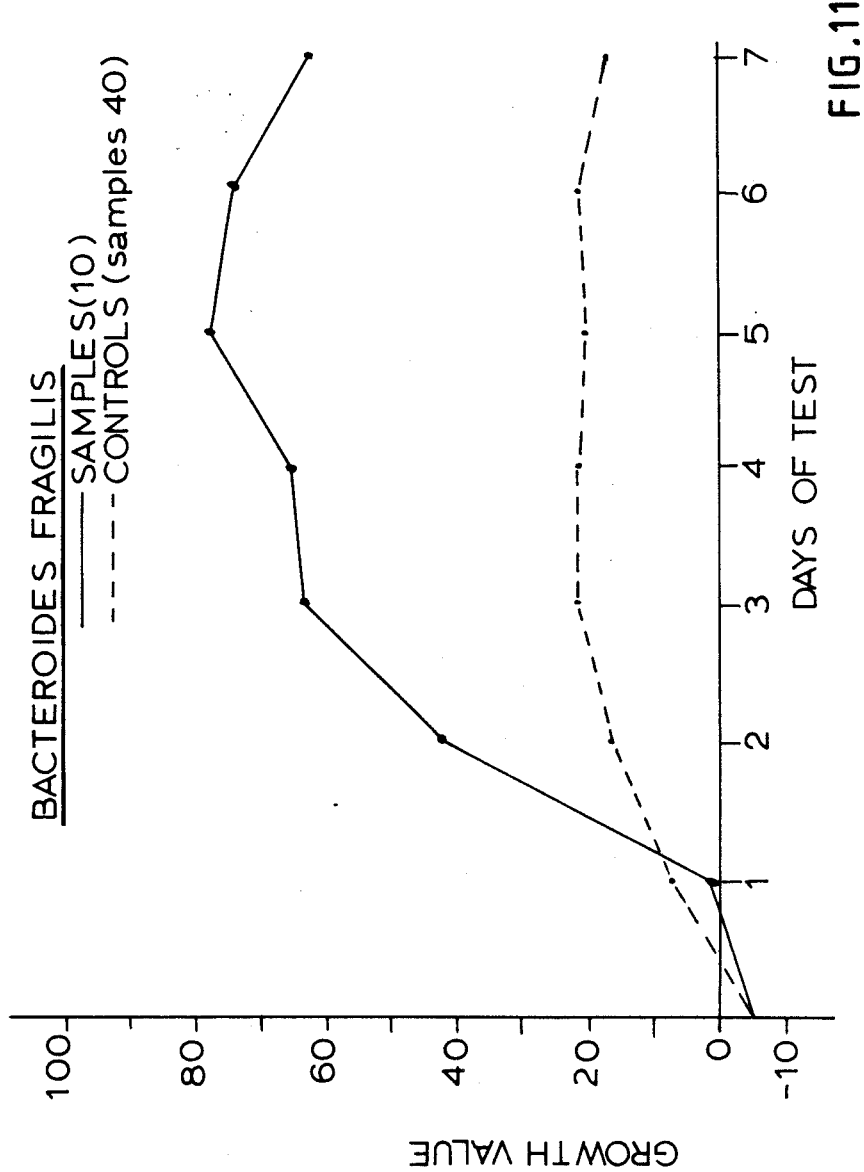

FIG. 11 is a graph depicting results of an infrared detection study conducted with the fastidious microorganism *Bacteroides fragilis* tested anaerobically.

Figure 12:
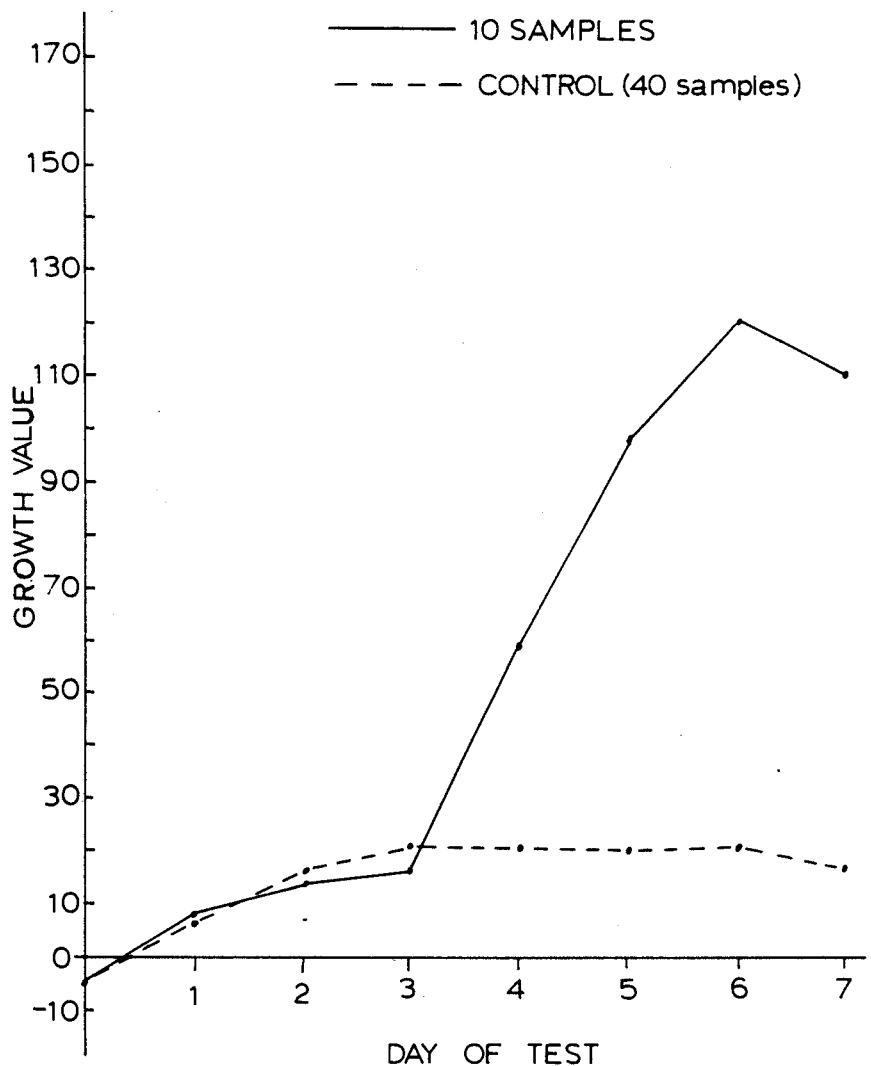

FIG. 12 is a graph depicting results of an infrared detection study conducted with the fastidious microorganism *Bacteroides vulgatus*.

In FIGS. 13–26, the plot defined by closed circle points represents the average of 8 inoculated samples detected by the infrared method of the invention; the plot defined by the closed triangle points represent the average of eight inoculated samples detected by commercial radiometric detection methods; the plots defined by the open circle and open triangle points are the average of 8 uninoculated blood control samples detected by infrared and radiometric methods, respectively. The → indicates the positive detection threshold.

Figure 13:
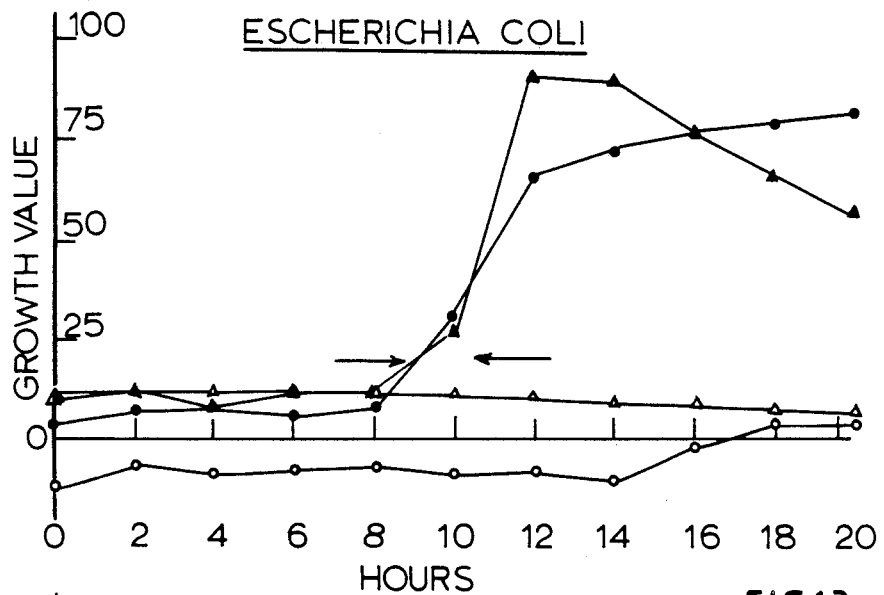

FIG. 13 is a graph presenting the results of a kinetic detection study comparing infrared detection response to that of a conventional radiometric detection system as a function of incubation time for the microorganism *Escherichia coli* tested aerobically.

Figure 14:
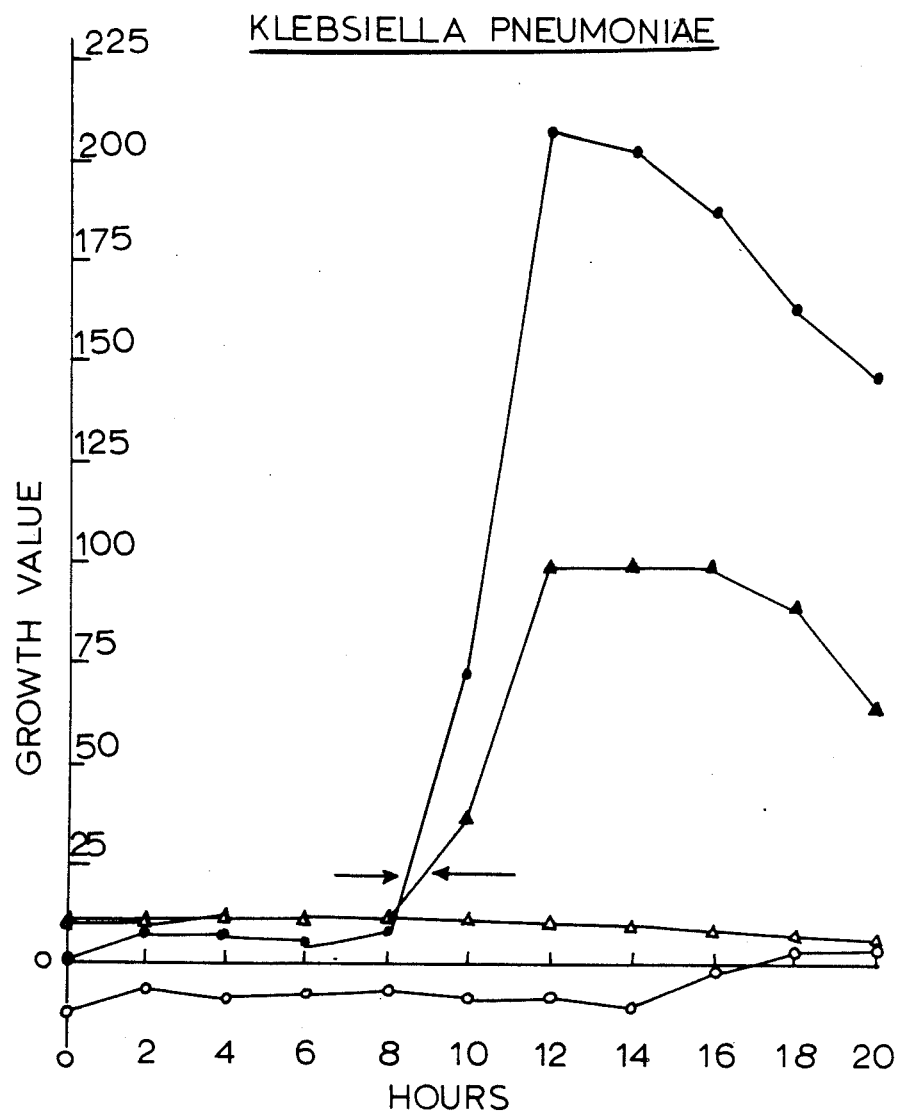

FIG. 14 is a graph presenting the results of a kinetic detection study comparing infrared detection response to that of a conventional radiometric detection system as a function of time for the microorganism *Klebsiella pneumoniae* tested aerobically.

Figure 15:
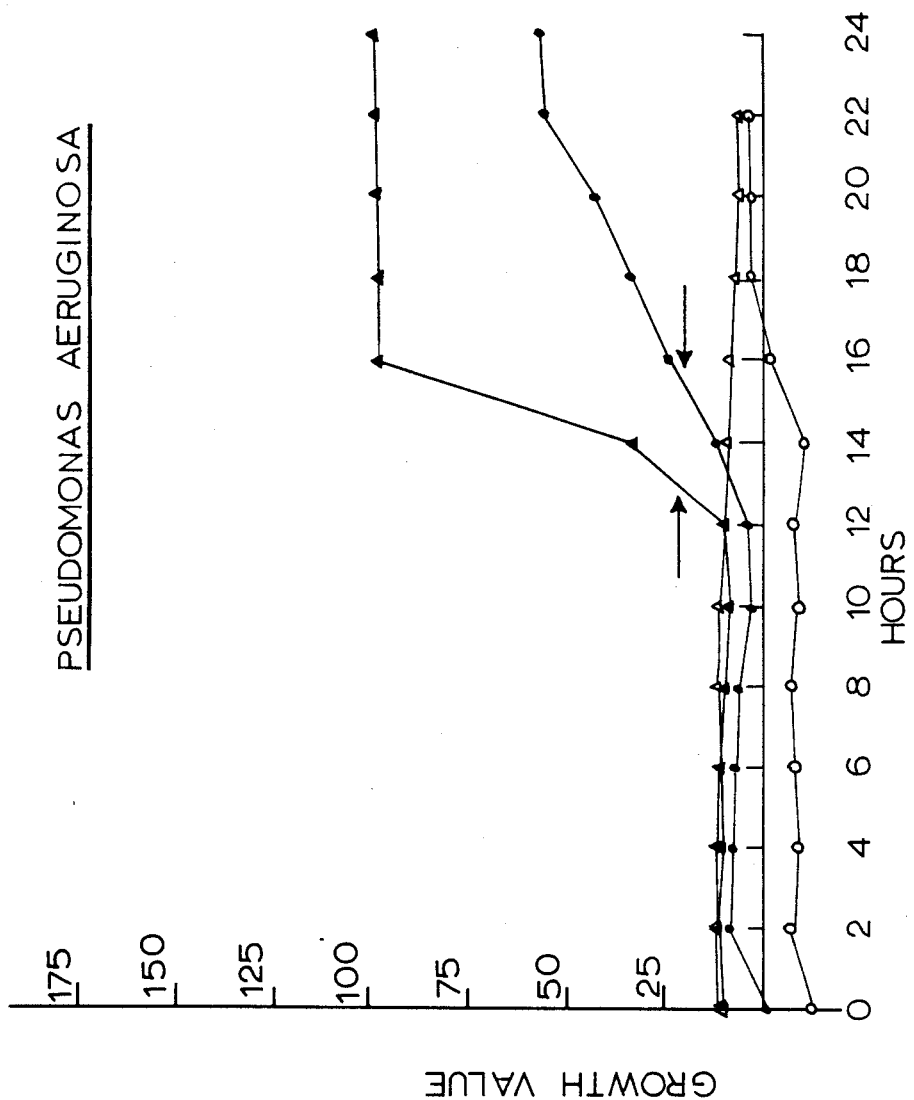

FIG. 15 is a graph presenting the results of a kinetic detection study comparing infrared detection response to that of a conventional radiometric detection system as a function of incubation time for the microorganism *Pseudomonas aeruginosa* tested aerobically.

Figure 16:
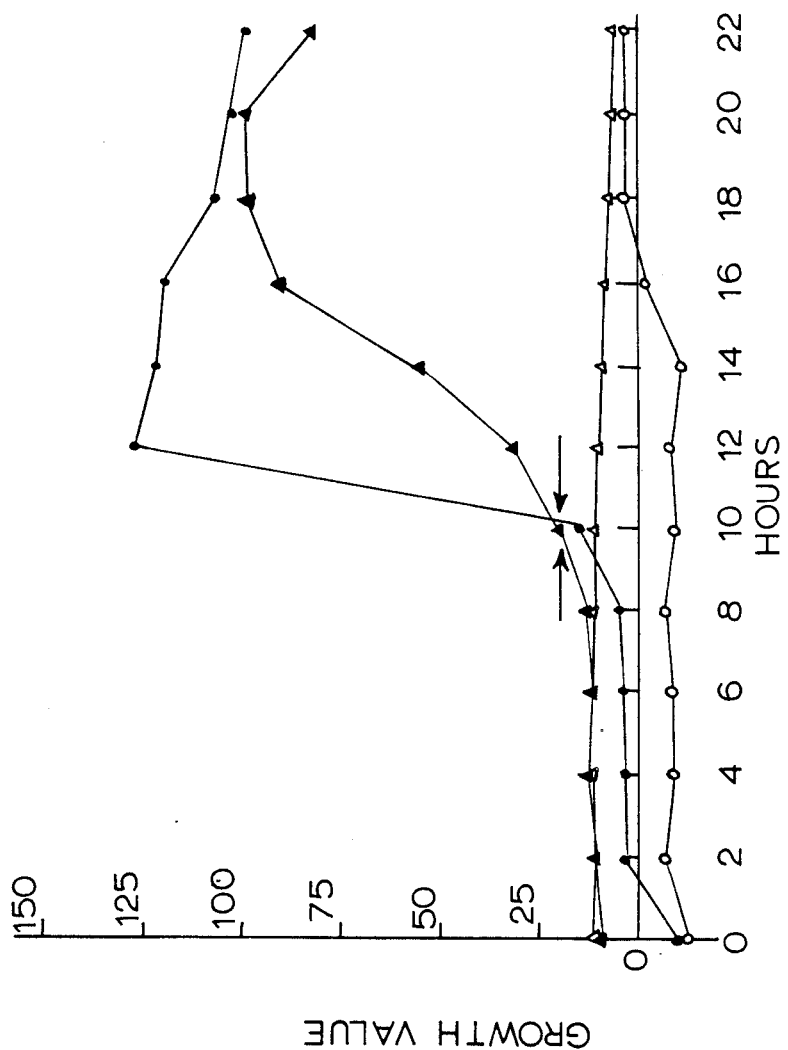

FIG. 16 is a graph presenting the results of a kinetic detection study comparing infrared detection response to that of a conventional radiometric detection system as a function of incubation time for the microorganism *Staphylococcus aureus* tested aerobically.

Figure 17:
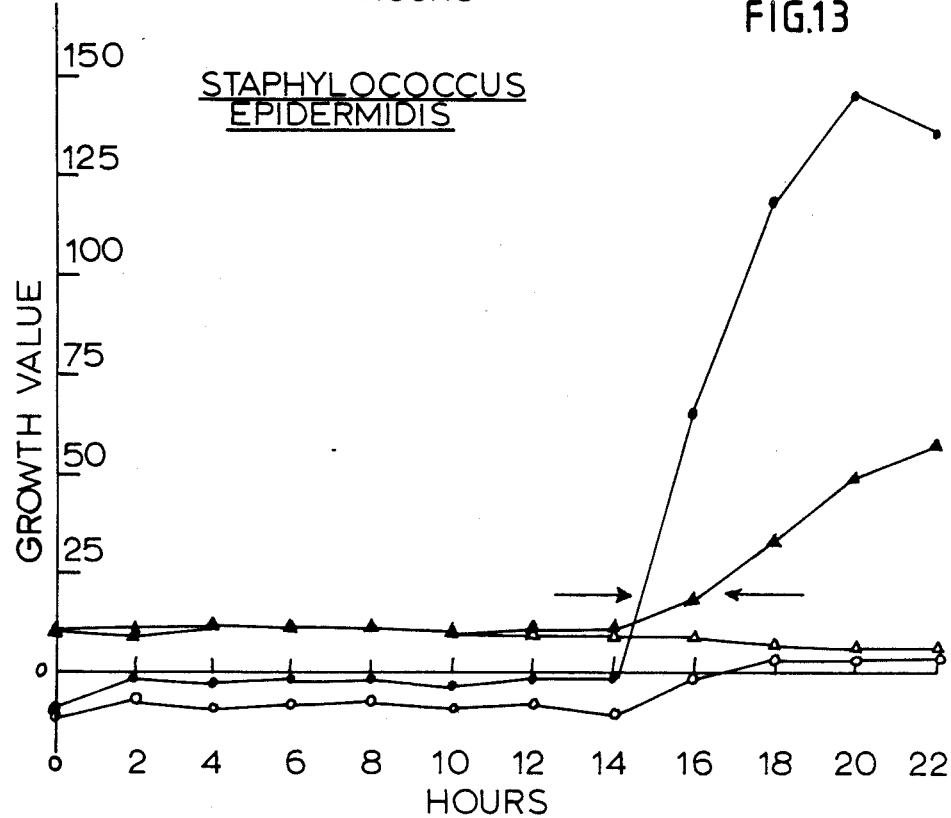

FIG. 17 is a graph presenting the results of a kinetic detection study comparing infrared detection response to that of a conventional radiometric detection system as a function of time for the microorganism *Staphylococcus epidermidis* tested aerobically.

Figure 18:
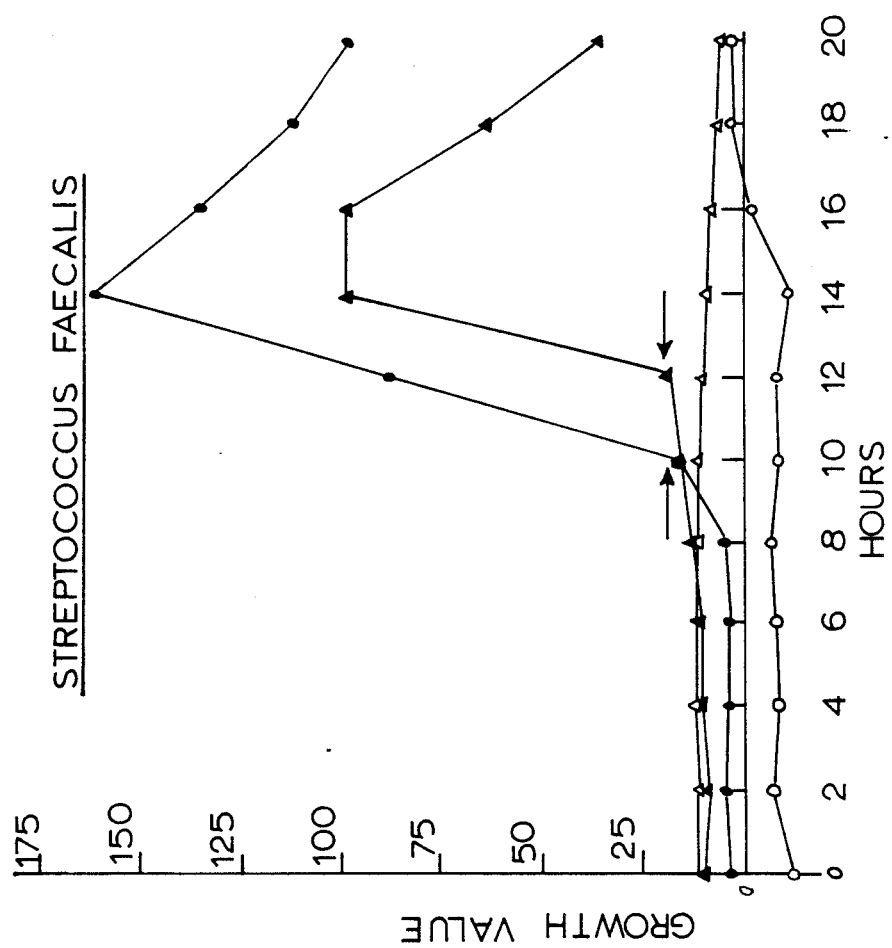

FIG. 18 is a graph presenting the results of a kinetic detection study comparing infrared detection response to that of a conventional radiometric detection system as a function of incubation time of the microorganism *Streptococcus faecalis* tested aerobically.

Figures 19, 20:
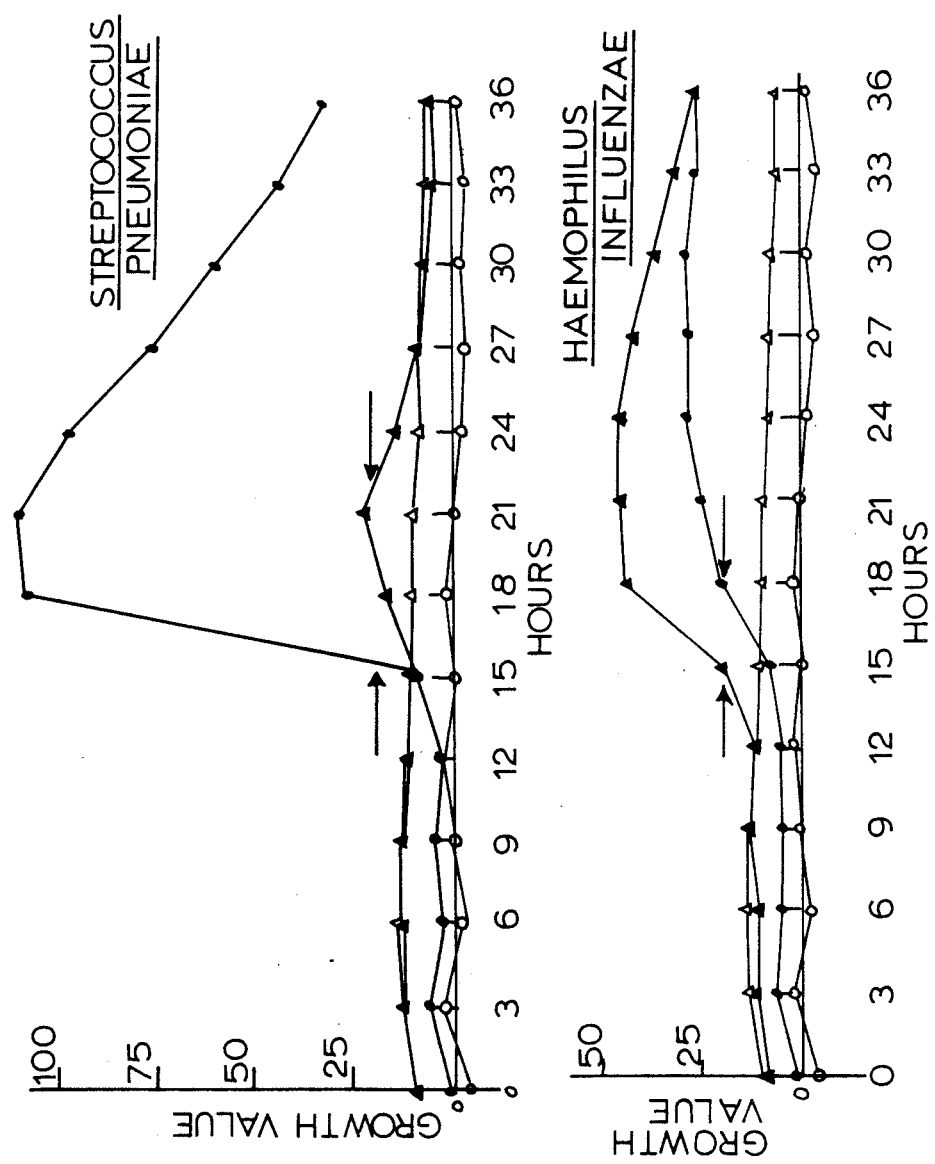

FIG. 19 is a graph presenting the results of a kinetic detection study comparing infrared detection response to that of a conventional radiometric detection system as a function of time for the microorganism *Streptococcus pneumoniae* tested aerobically.

FIG. 20 is a graph presenting the results of a kinetic detection study comparing infrared detection response to that of a conventional radiometric detection system as a function of incubation time for the microorganism *Haemophilus influenzae* tested aerobically.

Figure 21:
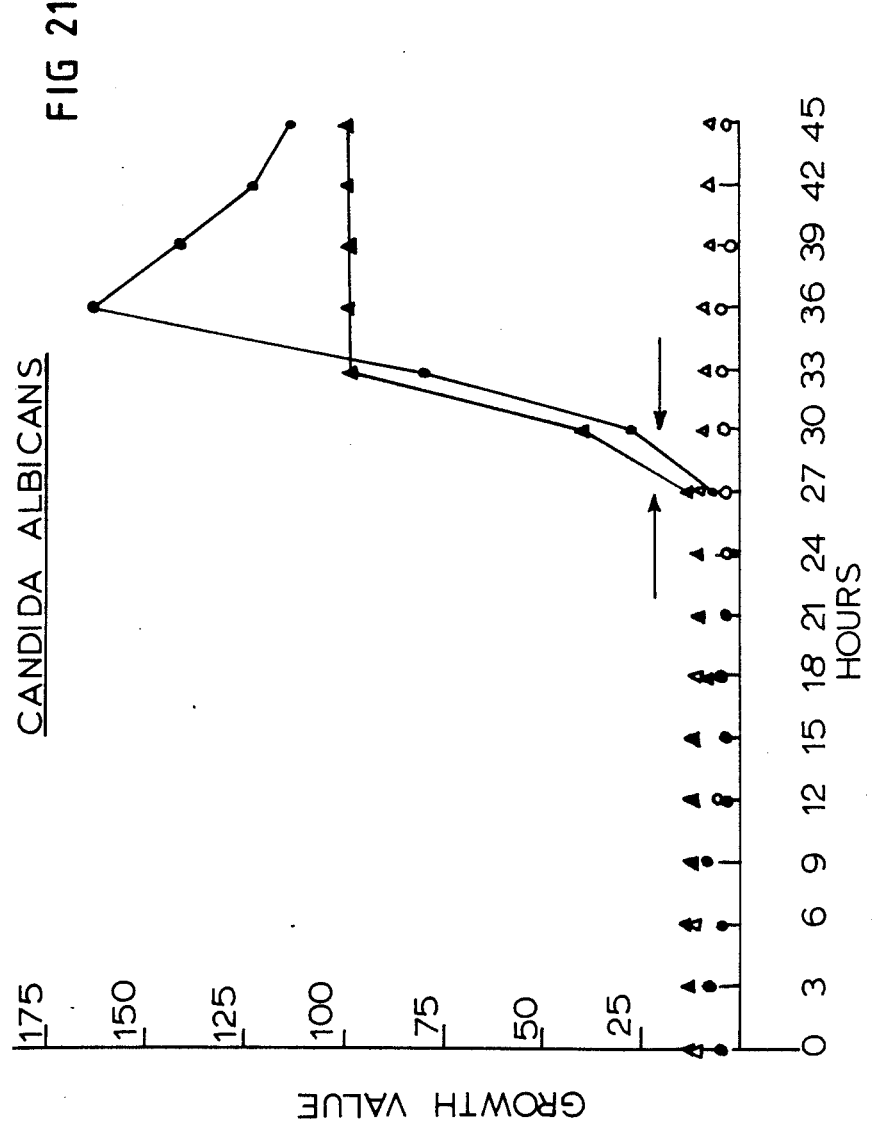

FIG. 21 is a graph presenting the results of a kinetic detection study comparing infrared detection response to that of a conventional radiometric detection system as a function of time for the microorganism *Candida albicans* tested aerobically.

Figure 22:
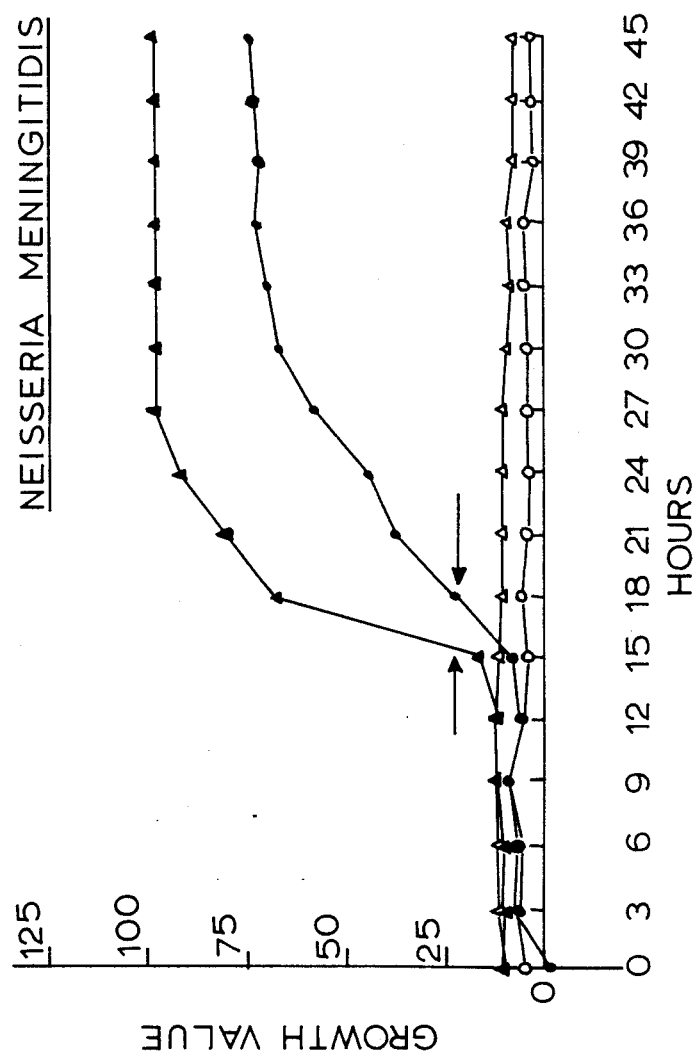

FIG. 22 is a graph presenting the results of a kinetic detection study comparing infrared detection response to that of a conventional radiometric detection system as a function of incubation time for the microorganism *Neisseria meningitidis* tested aerobically.

Figure 23:
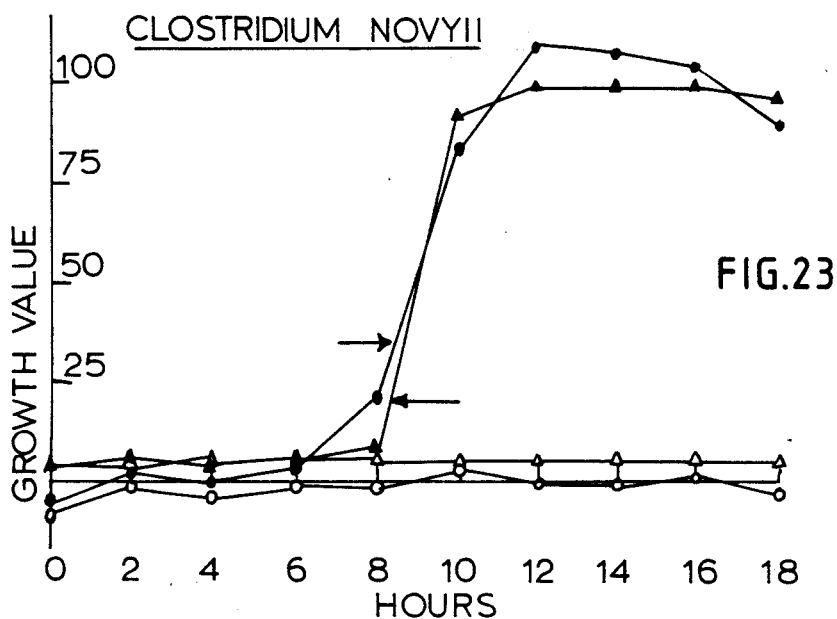

FIG. 23 is a graph presenting the results of a kinetic detection study comparing infrared detection response to that of a conventional radiometric detection system as a function of time for the microorganism *Clostridium novyii* tested anaerobically.

Figure 24:
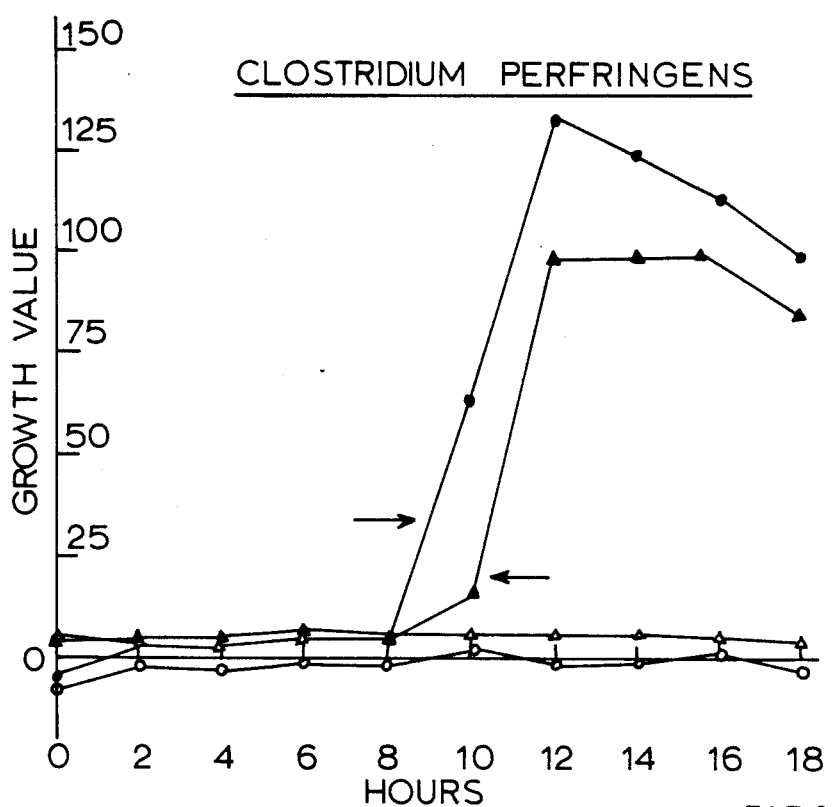

FIG. 24 is a graph presenting the results of a kinetic detection study comparing infrared detection response to that of a conventional radiometric detection system as a function of time for the microorganism *Clostridium perfringens* tested anaerobically.

Figure 25:
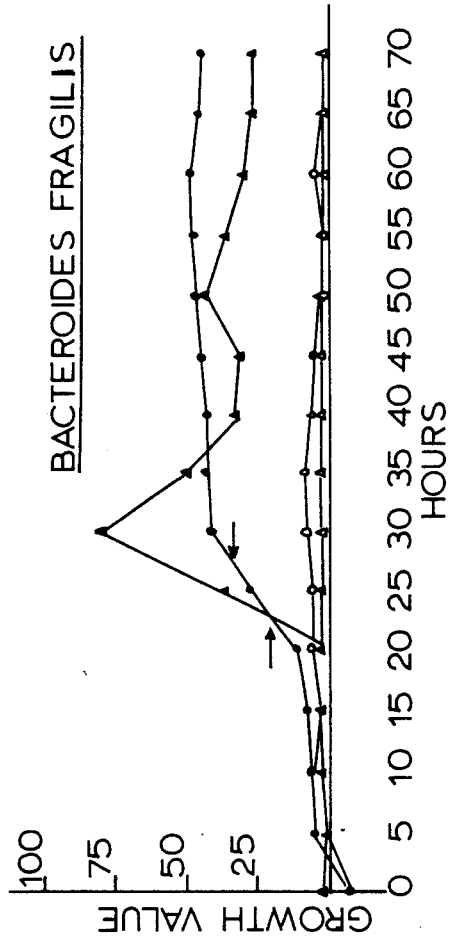

FIG. 25 is a graph presenting the results of a kinetic detection sutdy comparing infrared detection response to that of a conventional radiometric detection system as a function of time for the microorganism *Bacteroides fragilis* tested anaerobically.

Figure 26:
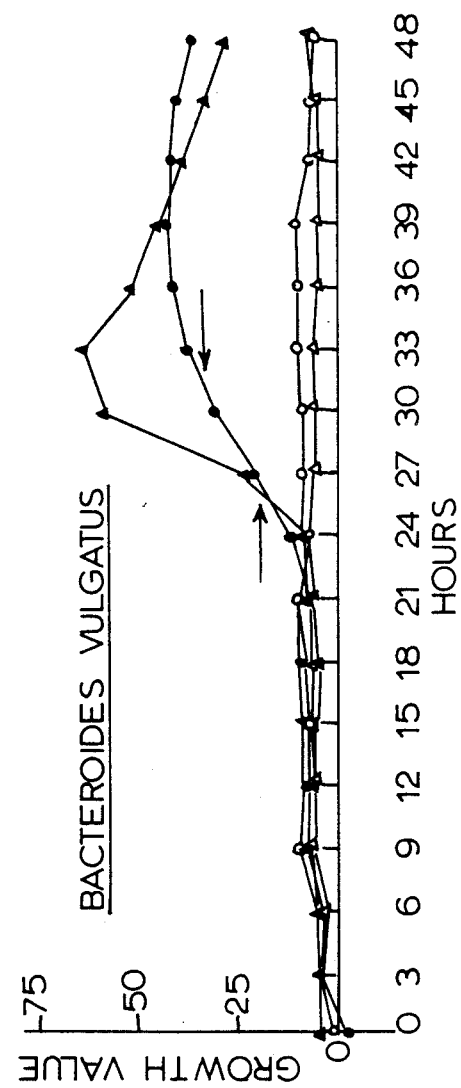

FIG. 26 is a graph presenting the results of a kinetic detection study comparing infrared detection response to that of a conventional radiometric detection system as a function of time for the microorganism *Bacteroides vulgatus* tested anaerobically.

Figure 27:
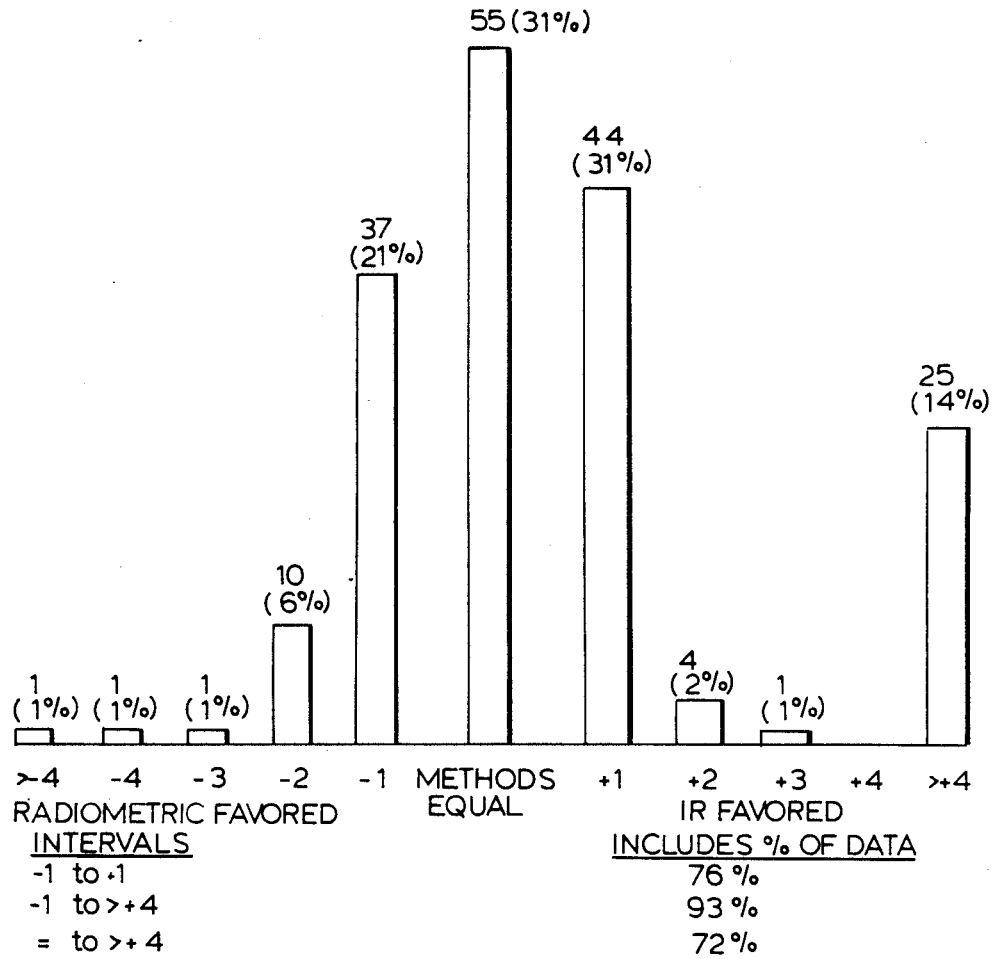

FIG. 27 is a bar graph depicting time-to-detection differences between matched container pairs studied kinetically to compare infrared detection to that of a conventional radiometric system. Results are shown in terms of test interval time differences between the two systems.

Figure 28:
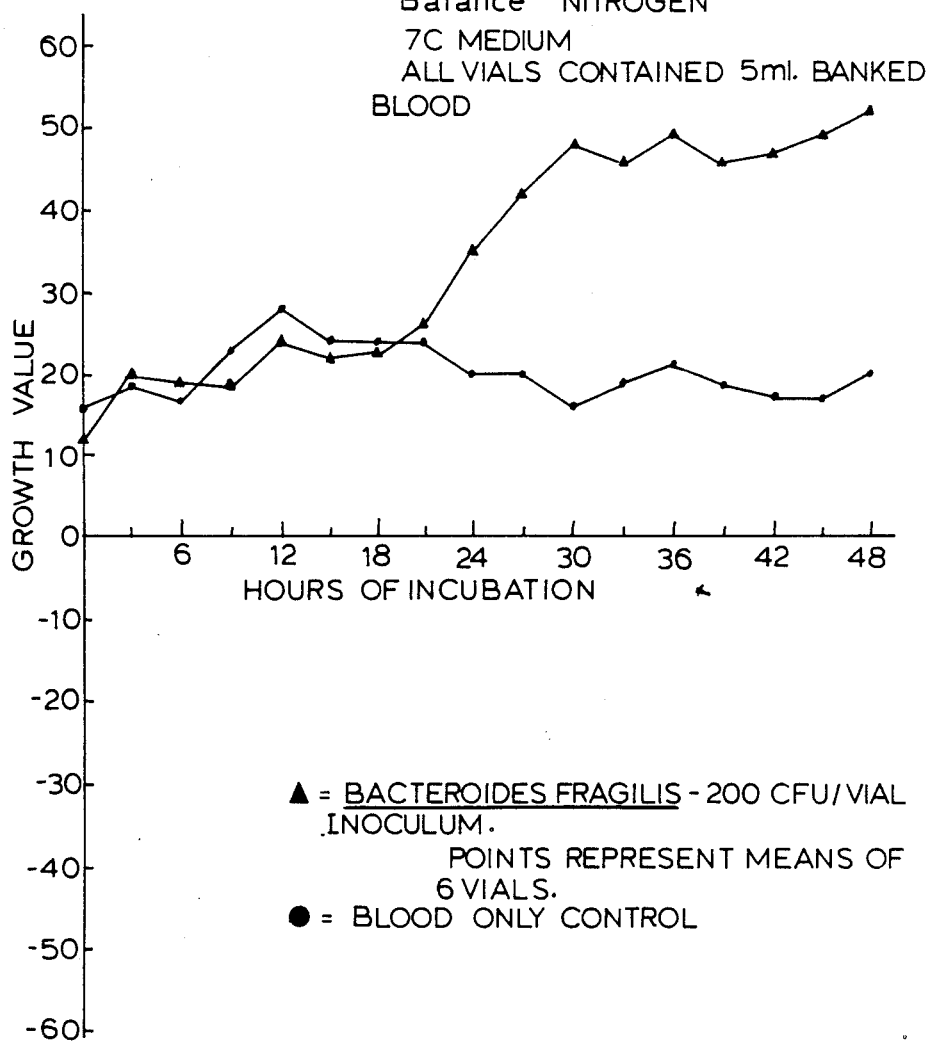

FIG. 28 is a graph presenting infrared growth response of the anaerobic microorganism *Bacteroides fragilis* as compared to the response of a sterile control when the apparatus culture gas employed contains no carbon dioxide.

Figure 29:
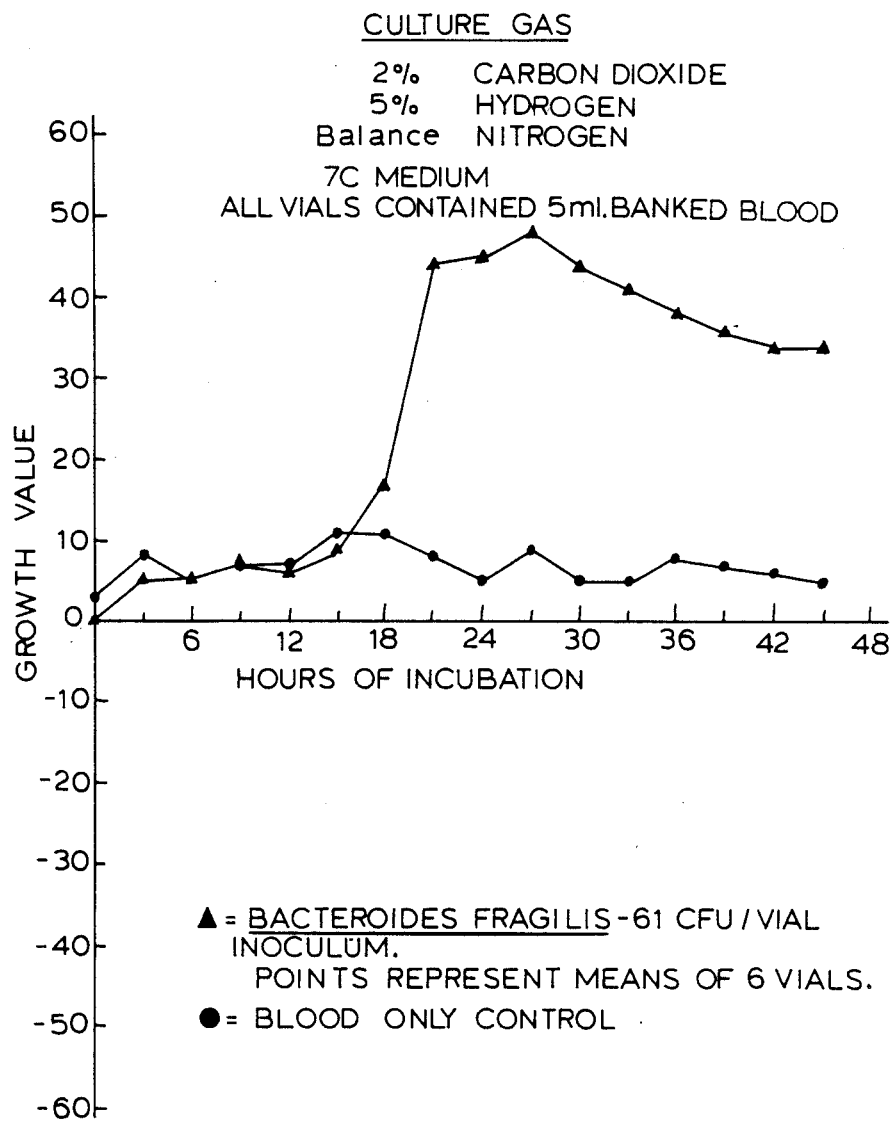

FIG. 29 is a graph presenting infrared growth response of the anaerobic microorganism *Bacteroides fragilis* as compared to the response of a sterile control when the apparatus culture gas employed contains 2% carbon dioxide.

Figure 30:
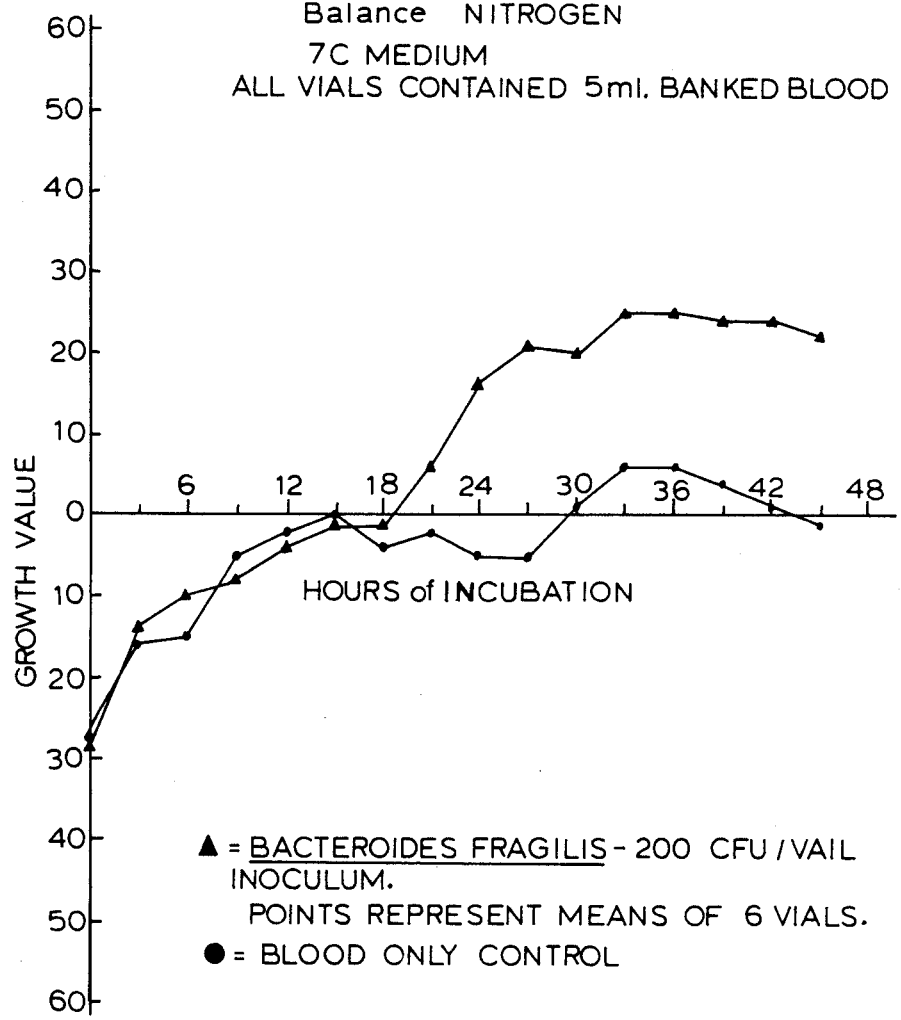

FIG. 30 is a graph depicting infrared growth response of the anaerobic microorganism *Bacteroides fragilis* as compared to the response of a sterile control when the apparatus culture gas employed contains 5% carbon dioxide.

Figure 31:
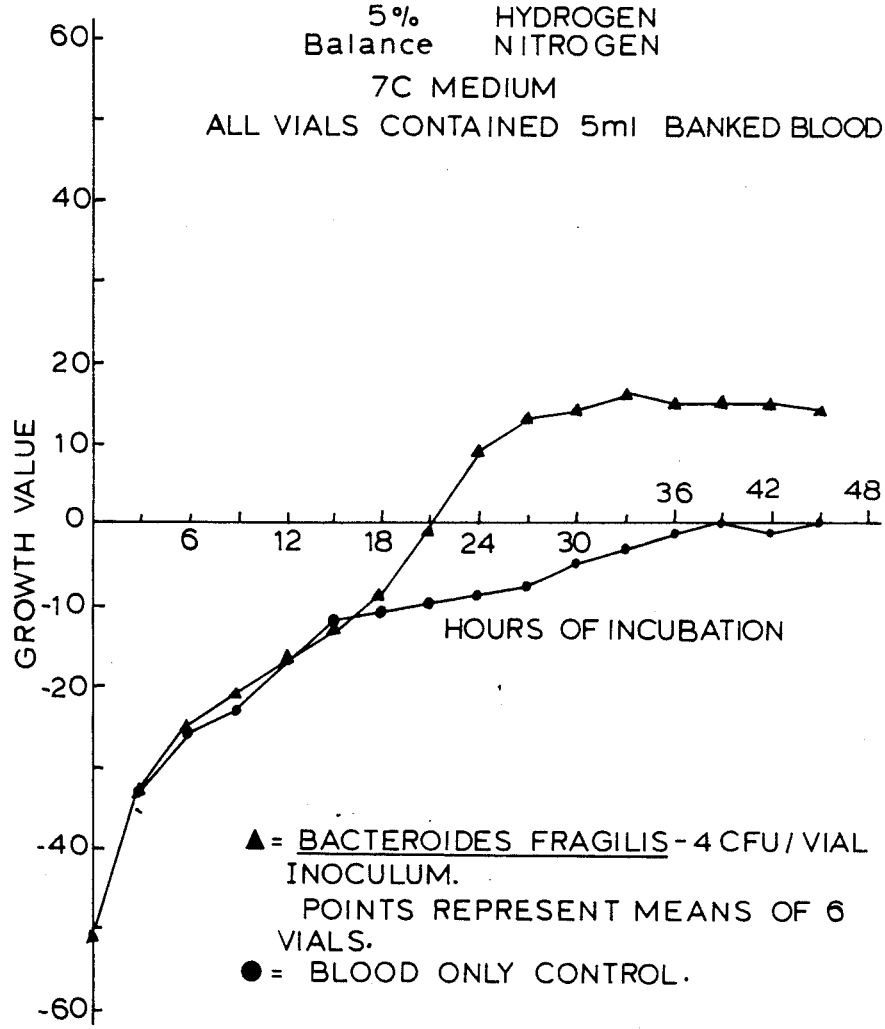

FIG. 31 is a graph presenting infrared growth response of the anaerobic microorganims *Bacteroides fragilis* as compared to the response of a sterile control when the apparatus culture gas employed contains 10% carbon dioxide.

Figure 32:
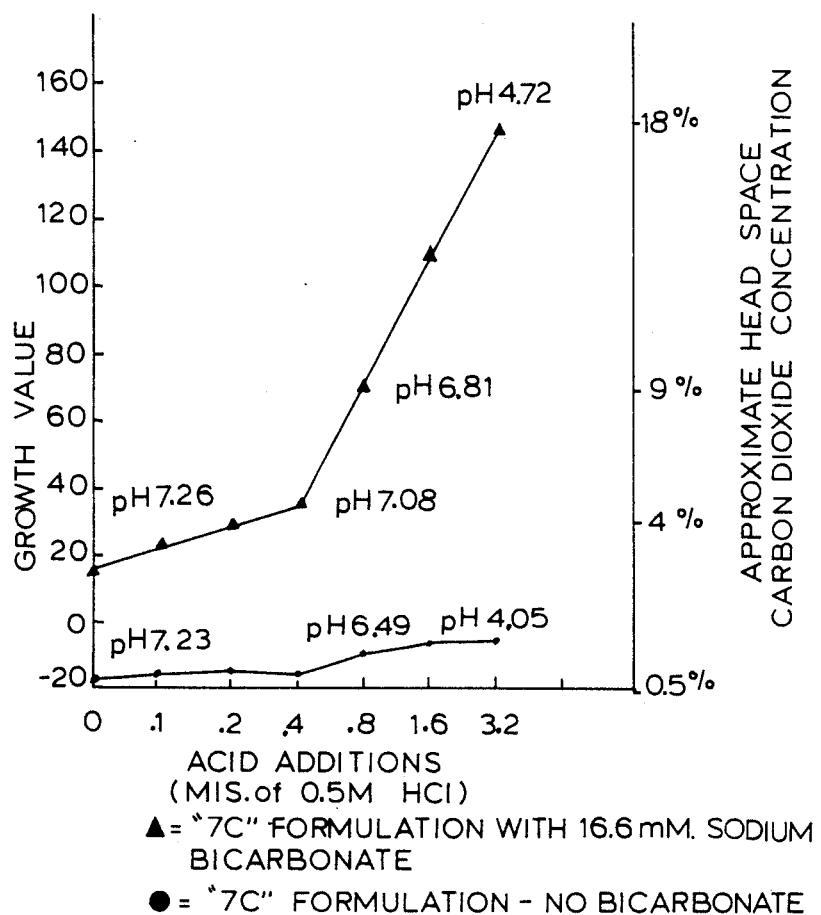

FIG. 32 is a graph presenting carbon dioxide liberation from bicarbonate supplemented anaerobic medium as a function of hydrochloric acid addition.

Figure 33:
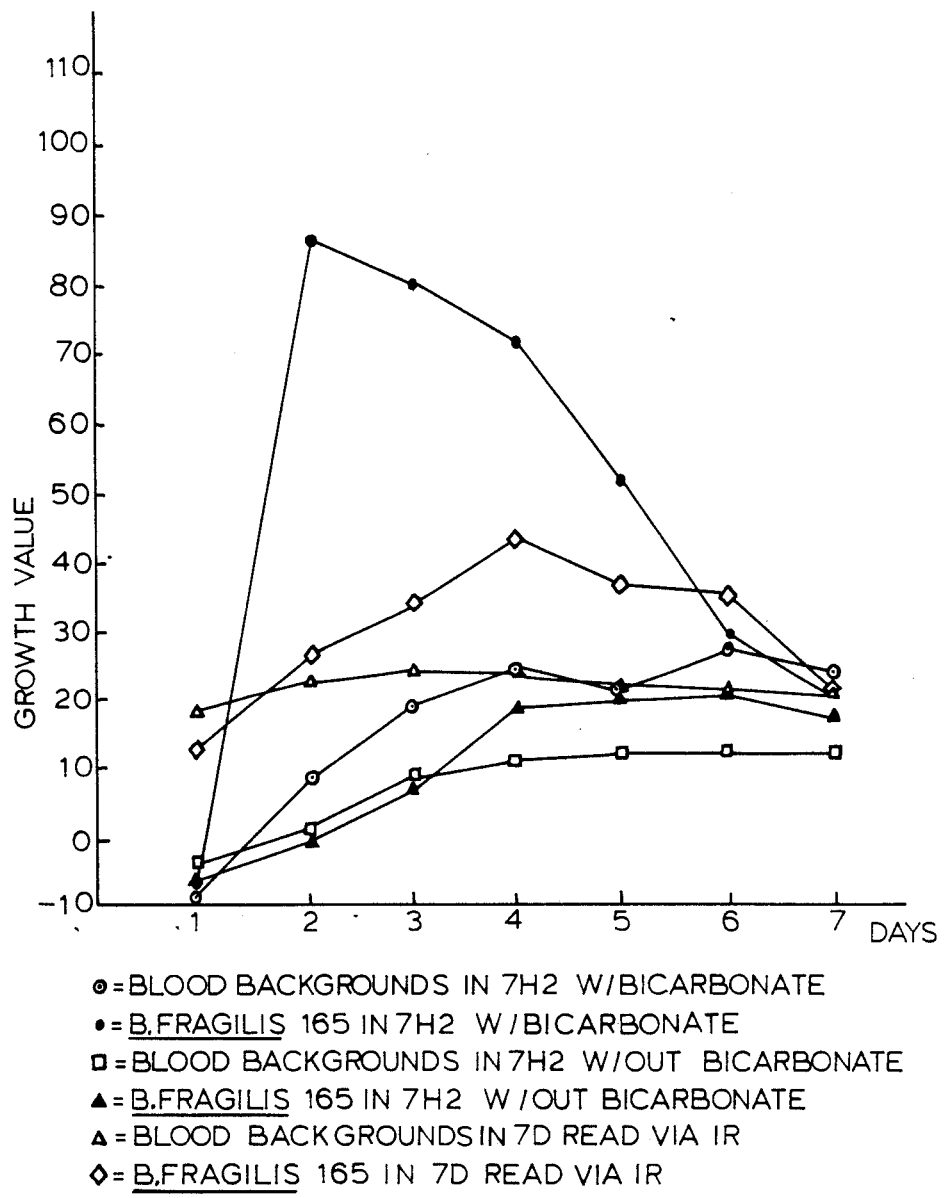

FIG. 33 is a graph of infrared detection response as a function of incubation time for the microorganism *Bacteroides fragilis* tested with and without bicarbonate supplementation of the growth medium.

DETAILED DESCRIPTION OF THE PREFERRED EMBODIMENTS

Figure 1:
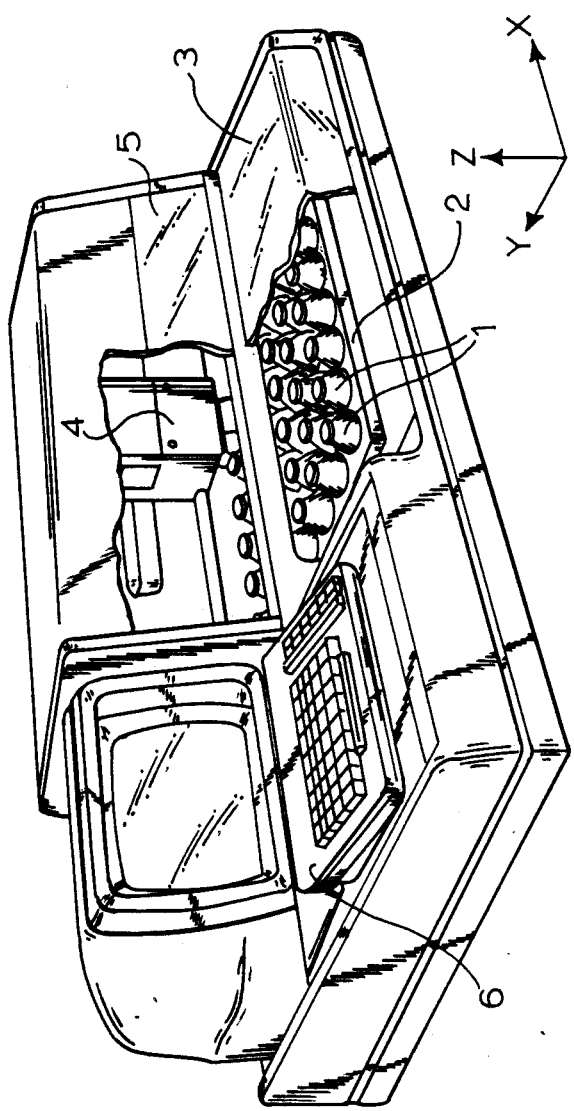
FIG. 1 is a pictorial view of the apparatus used in the practice of the disclosed invention.

A detection apparatus embodying the principles and concepts of the invention is broadly depicted in FIG. 1. Containers 1 to be tested for biological activity are held and arranged in rectangular trays 2 placed in position on the test bed. Transparent hinged dust cover 3 protects containers under test from external contamination and provides an operator work surface. Test head assembly 4, located behind user-access cover 5, traverses the Y-axis of the tray, testing each container present in sequence for head space gas carbon dioxide content. Upon completion of each row of container tests, the tray is indexed under the test head to align the next column of containers for testing. The apparatus is microprocessor-based, providing all operational control and user interface via CRT terminal 6. Test results and other information of operator interest is also available on an external printer (not shown).

The apparatus is particularly useful in providing early detection of the general presence of most medically significant bacteria in materials such as blood, urine, spinal fluid, synovial fluid, water samples and the like. The presence of such bacteria is readily detected by measuring the amount of $CO_2$ generated when a material to be analyzed is placed into a growth medium including a carbon source or sources which are metabolized to produce $CO_2$ and the medium with sample therein is thereafter incubated. A concentration of $CO_2$ in the sample of the head space gas removed from above the medium being significantly greater than present in the selected culture gas is an indication of the presence of microorganisms in the original sample of material.

Figure 2:
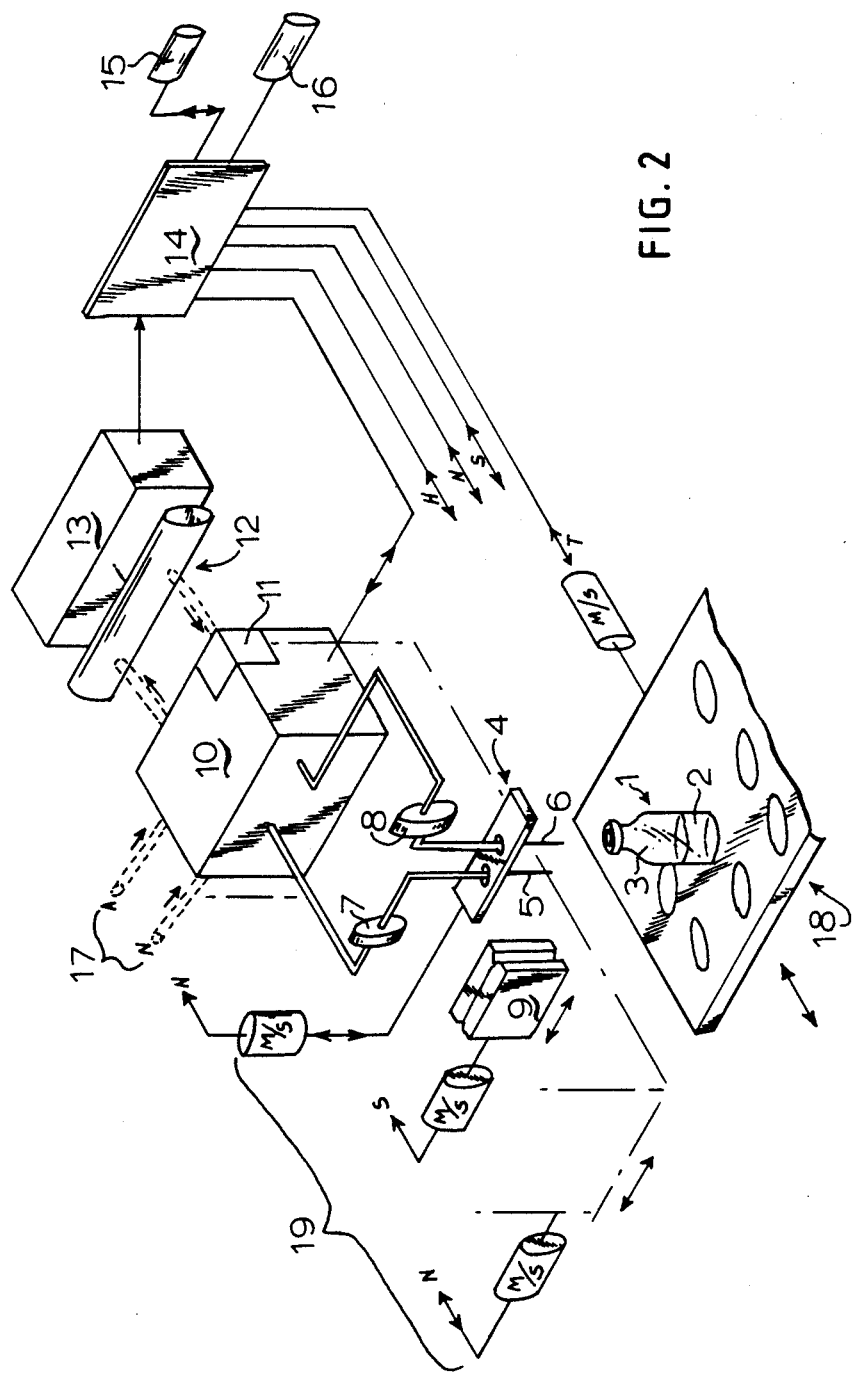
FIG. 2 is a schematic view of the main components comprising the disclosed apparatus.

FIG. 2 presents the major parts of the apparatus in schematic form. A sample of material to be analyzed, such as blood or urine or the like, is placed into a sterile culture container 1 fitted with a self-sealing rubber septum and aluminum closure. Present in the container is suitable growth medium 2, buffered to maintain the desired pH and to produce the desired concentration of $CO_2$ in the head space 3 above the medium. The container is then incubated under conditions promoting biological activity. At suitable intervals, needle set 4 is driven down to penetrate the septum of a positioned vial with two hollow stainless steel pencil-point needles 5, 6. The pneumatic system 10 including pump 11 recirculates the container head space gas up through needle 5, through submicron filter 7, through the measurement sample cell 12 of an infrared $CO_2$ analyzer 13, returning the gas to the vial via submicron filter 8 and needle 6. The resulting $CO_2$ reading is digitized and recorded by the data system/controller 14. Results are presented by means of a CRT terminal 15 or printer 16 connected to the data system/ controller.

Following each test, the needle set is withdrawn from the container, and aerobic or anaerobic culture gas from external sources 17 is used to purge the needle set, pneumatic system, and infrared sample cell 12 of head space gas left in the measurement system as a consequence of the test. Needle heater 9 is then brought to a position enclosing needles 5 and 6, heating them to a temperature sufficient to greatly diminish any chance that viable organisms lodged in or on either of the needles can be transferred to succeeding containers, resulting in cross-contamination. Testing of multiple containers in automated fashion is facilitated through provision of a tray 18 fabricated to contain a multiplicity of containers in a rectangular array. Energizing and sensing components are provided to move the tray along the Y-axis of the instrument test bed. Components 4 through 9 comprise the test head assembly 19, which includes sensing and motive components to translate the assembly as a unit along the X-axis of the test bed.

Because the head space gas $CO_2$ concentration present in a sterile vial at incubation temperature is controlled by chemical equilibrium established during medium formulation and container filling during manufacture, and because the external culture gas $CO_2$ concentration is chosen to be substantially equal to the equilibrium concentration of $CO_2$ present in the sterile container head space, correction for the head space $CO_2$ concentration may be achieved by subtracting the value measured for the culture gas. Containers incubated and tested which contain sterile material will thus have corrected $CO_2$ readings very nearly zero, while those containers exhibiting biological activity will have corrected readings greater than zero by a statistically significant amount. The corrected reading units, scaled to resemble readings obtained with a radiometric BACTEC instrument commercially available from Johnston Laboratories Division of Becton Dickinson and Company, Cockeysville, Md., have been termed "Growth Value Units" abbreviated "GV".

Figure 3:
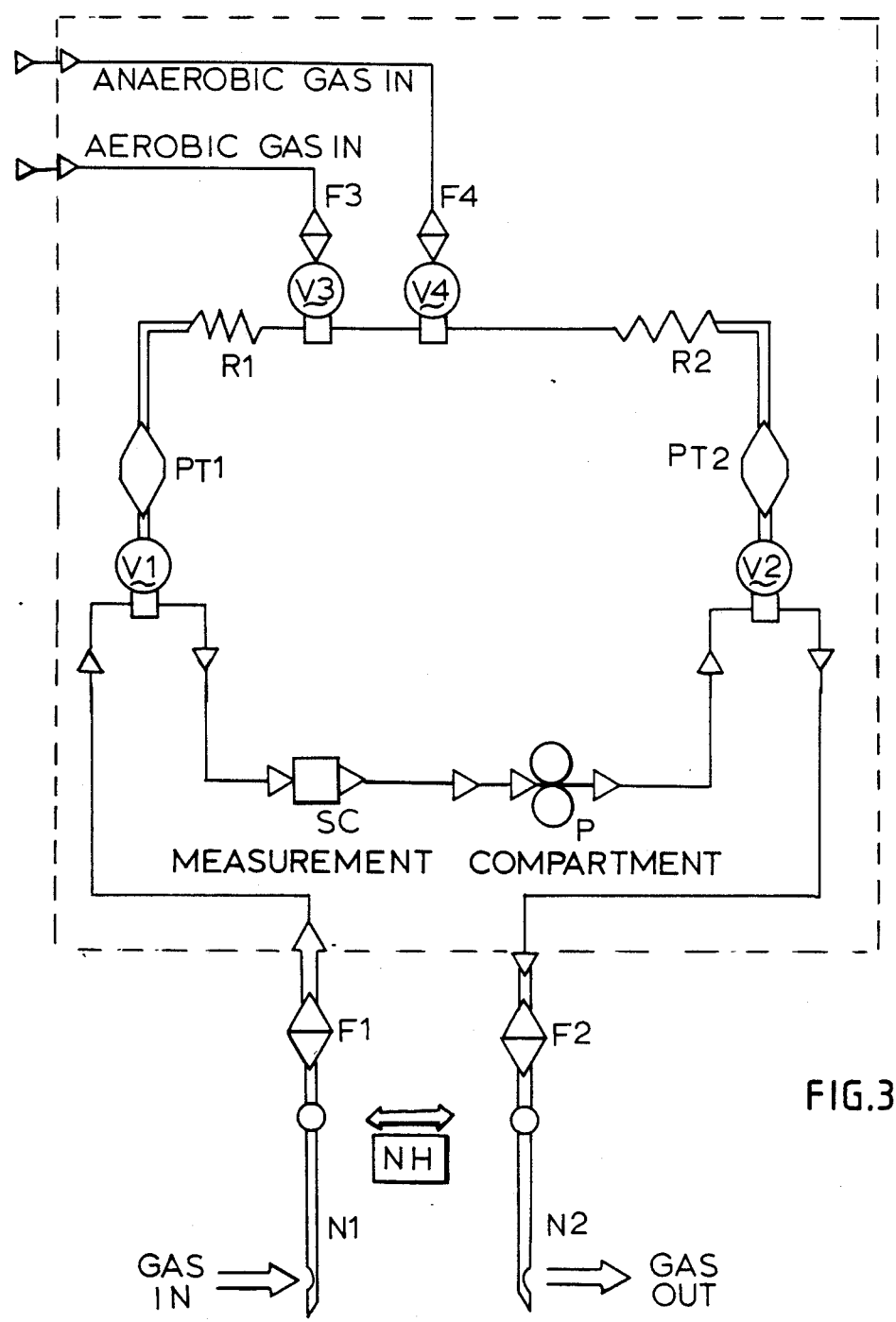
FIG. 3 is a schematic view of the pneumatic system utilized in the disclosed apparatus.

The pneumatic system of the apparatus is detailed schematically in FIG. 3. Culture gas from an external, pressure-regulated source for the testing of containers of aerobic media is filtered by particulate filter F3 and is then supplied to the remainder of the system via electrically operated solenoid valve V3. Anaerobic culture gas for the testing of containers with anaerobic cultures is similarly supplied and filtered by F4 and controlled by solenoid valve V4. Pneumatic resistances R1 and R2 provide flow-dependent pressure drops in each leg of the pneumatic circuit. Pressure transducers PT1 and PT2 are employed to sense operating pressures in each leg of the pneumatic circuit. Readings obtained during various portions of the operating cycle are used to insure proper operation of the apparatus and to provide adequate fault detection, should leaks, clogs, or pump failure occur. Solenoid valves V1 and V2 serve to isolate the head space gas sampling loop from the remainder of the system. Diaphragm pump P serves to circulate head space gas around the sampling loop during testing and to provide the requisite pressure differentials for system purging and performance testing.

During a container test for head space $CO_2$ content, needles N1 and N2 pierce the elastomeric seal of culture container CC. Head space gas is drawn up through needle N1 through sterilizing/ droplet filter F1, then through the measurement cell SC of a non-dispersive infrared analyzer by the action of pump P. Head space gas is returned to the container through assembly NH serves to aid in the prevention of biological contamination of succeeding culture containers due to non-sterile foreign materials collected in or on the sampling needles as a consequence of head space sampling of positive cultures, performance testing of measurement system function, or exposure of the needle assembly to ambient atmosphere during periods when the apparatus is idle. The pneumatic system, together with the non-dispersive infrared carbon dioxide analyzer, comprise the measurement system of the apparatus. A suitable non-dispersive infrared analyzer is the Series V $CO_2$ IR Analyzer (Sensors, Inc., Saline M148176). Suitable solenoid valves are provided by ITT General Controls (Glendale, Calif. 91201). Pressure transducers appropriate for the referenced pressure measurements may be obtained from MicroSwitch Division of the Honeywell Corporation (Freeport, Ill. 61032). A diaphragm pump suitable for pneumatic system application consists of a pump head, model N05 (KNF Neuberger, Inc., Princeton, N.J. 08540) coupled to a P/N DB31D-12 motor (Eastern Air Devices, Dover, N.H. 03820. Although the choice and arrangement of components comprising the measurement system described herein are suitable for the practice of the present invention, other components and arrangements may be used, as will occur to those skilled in the art.

The complete testing of an array of sample containers for biological activity as taught by the method disclosed herein, including performance testing and needle heating, comprises one test cycle of the apparatus as accomplished by the measurement system and controlled by the data system. The complete test cycle is comprised of a preflush subcycle, instituted for each array of containers to be tested, and a container test subcycle, activated to test each container in the array individually. Because the specifics of the apparatus test cycle are to a large extent dependent upon the choice of measurement system components and the configuration of the apparatus control software, the following discussion of test cycle function is provided as an example of the various apparatus functions required for practice of the method as implemented using a prototype version of the disclosed apparatus.

Various operational performance tests of the pneumatic system and IR analyzer are conducted during the test cycle activity under the direction of the data system/controller. The ability to test all pertinent components of the measurement system is in a large part responsible for the relative complexity of the pneumatic system beyond those components enclosed within the head space gas sampling loop (N1, F1, SC, P, F2, N2 in FIG. 3).

Figure 4:
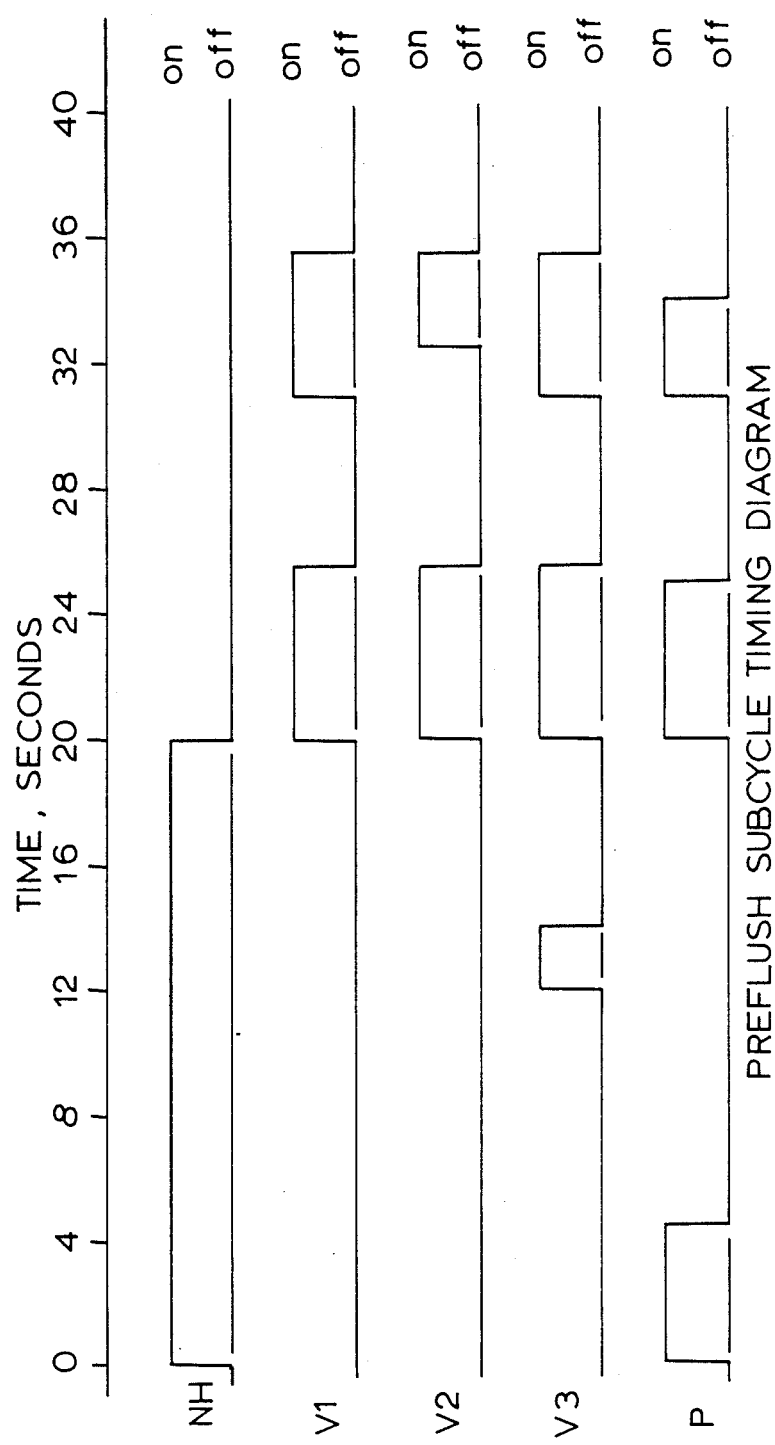
FIG. 4 is a timing diagram describing the pneumatic system preflush cycle.

The preflush subcycle is best understood with reference to the timing diagram presented in FIG. 4 in conjunction with the pneumatic system diagram of FIG. 3. Upon initiation of the test cycle, the preflush subcycle begins with the test head and associated needle assembly raised, and hence exposed to the ambient, room air atmosphere. All solenoid valves are closed. It is assumed that aerobic containers are to be tested, hence culture gas will be supplied via V3 when needed. Pump P is energized briefly, so as to fill the sample cell SC of the IR analyzer with room air by flow through the needles N1 and N2. The needle heater NH is also energized at this time, in order to preheat the heater assembly for subsequent tests and to prevent biological contamination of the system from materials possibly deposited on the exposed needles. The analyzer is provided a brief period to stabilize, during which time the needle heater is extended to surround the needle assembly.

At the completion of the stabilization period, the analyzer output is read, and compared with ambient air high and low $CO_2$ limit values stored in the data system. Normal output permits testing to continue; an abnormal value aborts the test and issues a message for the operator to check the zero-adjust of the IR analyzer. Valve V3 is opened briefly at this time, and pressure transducers PT1 and PT2 are read and compared to stored parameters to ensure the presence of culture gas at the appropriate supply pressure as well as to test for proper pressure transducer function. The difference in transducer output is compared to a stored constant, and a warning message issued to service the pressure transducers if the stored value is exceeded. The output of PT1 is then compared to a second pair of constants for high and low limit, and high and low culture gas pressure warning messages are issued if the output does not fall between limits. Testing is discontinued in either case.

V3 is then closed to conserve culture gas while needle heating continues for a period sufficient to raise the needle block temperature to the desired value. Needle heating is then discontinued, retraction of the heater assembly begun, pump P is started, and valves V1, V2, and V3 are opened to permit culture gas flow through the pneumatic system, filling the IR sample cell SC and the pump, P1 with culture gas. Several seconds of gas circulation are provided to insure that the system has been purged and filled with culture gas. The transducers PT1 and PT2 are then read and the difference of their respective readings taken and compared with a previously stored limit to ensure proper pump operation. A normal difference permits testing to continue; an abnormal difference aborts testing and causes a warning message to be issued to check the pump and connecting tubing. Pump P is then stopped, followed by the closing of valves V1, V2 and V3.

The IR analyzer is permitted time to stabilize. The output of the IR analyzer is then read, the previously stored reading for ambient air subtracted, and the result compared to normal limit values for the selected culture gas. A normal result between limit values permits testing to continue; an abnormal result aborts testing and causes a warning message to be issued to check for either high or low $CO_2$ content of the culture gas and to check the measurement system. The reading of culture gas $CO_2$ content is also stored by the data system, and is used to correct measured head space gas vial test readings as taught by the disclosed method.

Pump P and valves V1 and V3 are then energized with V2 closed, permitting culture gas to exit from needles N1 and N2. Transducer PT2 is then read and compared to previously stored high and low limits to ensure that the culture gas pressure is neither too high nor too low. Abnormal test values cause the test to be aborted and warning messages to be issued to check the external culture gas source pressure, either high or low. The pump is then stopped, preventing further communication between the two legs of the system, and valve V2 is opened. With V1, V2 and V3 now open, culture gas flows through each leg of the pneumatic system, exiting needles N1 and N2. Tranducers PT1 and PT2 are again read and individually compared with stored values to ensure that the pressure drop across each needle and filter is within acceptable limits. Test failure causes further testing to be discontinued, with issuance of a warning message to check needles and filters for obstructions (high pressure) or to check all tubing connections (low pressure). Valves V1, V2 and V3 are then closed, completing the preflush subcycle.

Figure 5:
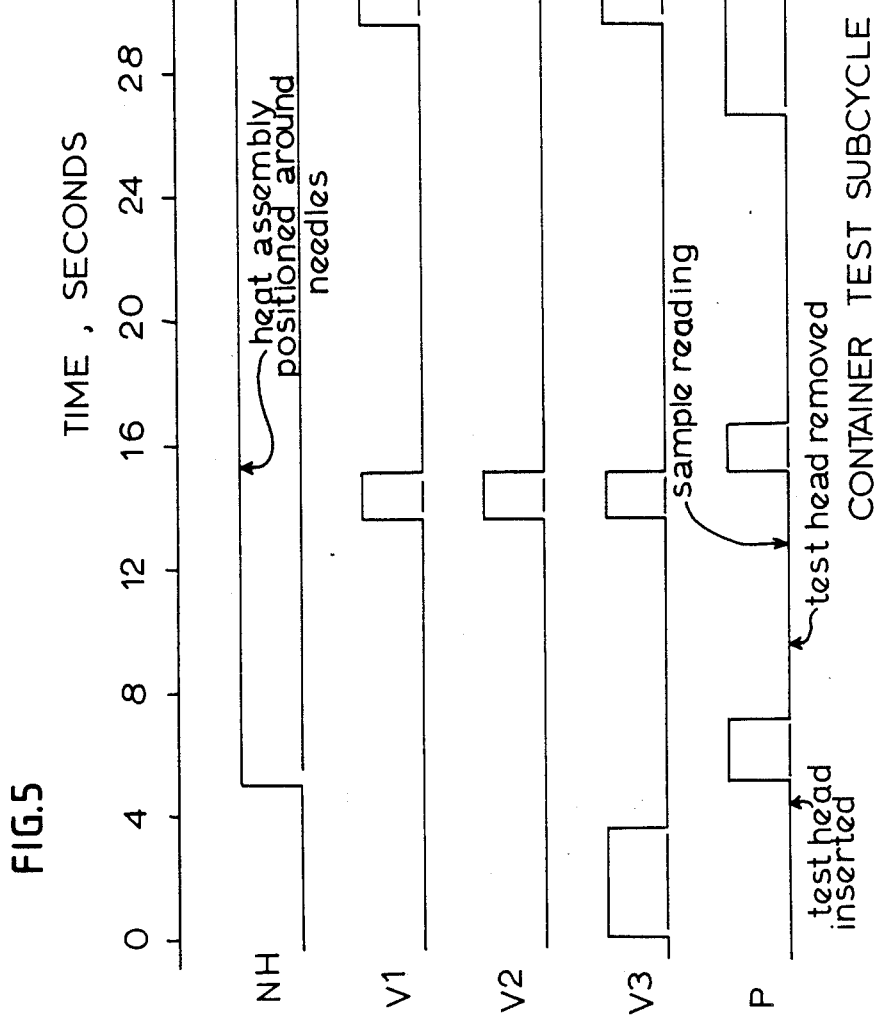
FIG. 5 is a timing diagram describing the pneumatic system container test subcycle.

The container test subcycle follows the preflush subcycle, and is repeated for each container to be tested. Apparatus timing during the test subcycle is presented in FIG. 5, referenced to the pneumatic system shown in FIG. 3. The subcycle is entered with all valves closed and the needle heater deenergized. The measurement system which includes the needles N1 and N2, the sample chamber SC and the connective piping contains pure culture gas as a consequence of preflush activity. Tray and test head motion are activated to bring the first container to be tested under the test head, as previously shown schematically in FIG. 2. Correct vial position is determined by various optical sensors (not shown) under data system control. Proper X, Y positioning defines zero time for the test subcycle. The previously selected culture gas source is used for either aerobic or anaerobic testing and compared against the encoded container tray to assure that the appropriate culture gas has been selected. Agreement permits testing to continue, while a mismatch aborts testing and issues a warning for culture gas selection.

Valve V3 is energized to admit culture gas to the system, and transducers PT1 and PT2 are read and the difference of their readings taken. A differential reading which exceeds the previously stored limit causes the issuance of a warning message to service the pressure transducers, while a reading from PT1 outside prescribed high and low limit values causes messages to be issued to check for either high or low culture gas pressure. Valve V3 is then closed. The test head assembly is then driven downward, causing needles N1 and N2 to penetrate the elastomeric container seal, gaining access to the container head space. Pump P is then energized, transferring head space gas to the sampling loop of the pneumatic system.

The closed-loop nature of head space gas circulation causes the head space gas to be diluted with culture gas by an amount dependent upon the relative volumes of the container head space and the sampling loop, in turn causing the measured $CO_2$ content to be different from the $CO_2$ concentration present in the head space prior to sampling. This unavoidable dilution must be minimized in order to preserve the efficacy of the test method. Ideally, the sampling loop volume is miniscule compared to the container head space volume, resulting in a negligible dilution of the head space gas upon circulation through the sampling loop. Practical considerations dictate that the obtainable minimum dilution is approximately 50 percent, a value obtained only through careful minimization of connection tubing lengths within the pneumatic system, choice of pump and solenoid valves for minimum dead volume, and the like.

In order to minimize measurement offset and to maximize test sensitivity for increases in head space $CO_2$ concentration due to biological activity, it is an important consideration of the present invention that the $CO_2$ concentration of the external culture gas be substantially equal to the head space $CO_2$ concentration of a sterile vial at incubation temperature prior to introduction of a sample to be tested. This consideration is important to the practice of the method disclosed herein.

The concentration of carbon dioxide in the culture gas is selected to be substantially the same as the concentration of carbon dioxide in the head space gas of the sealed vial prior to introduction and incubation of the sample. In general the anaerobic culture gas will have from about 1 to about 10 percent carbon dioxide, from about 0 to about 10 percent hydrogen and the balance nitrogen. In general, the aerobic culture gas will have from about 1 to about 10% carbon dioxide and the balance air. The concentration of $CO_2$ in the head space of a sterile vial is a function of the conditions under which the growth medium is added to the vial and the composition and amount of the growth medium. In one preferred form of the invention, the $CO_2$ concentration of the head space gas for a 60 ml vial filled with 30 ml of an anaerobic culture medium will be from about 3 to about 5 percent. All percentages expressed herein are volume percent unless specifically indicated otherwise. The same vial filled with 30 ml of an aerobic culture medium will ave a $CO_2$ concentration in the head space gas of from about 2 to about 3 percent.

The needle heater assembly NH is energized and the pump is run for a period of time sufficient to insure complete mixing of the culture gas and head space gas within the sampling loop and culture container. The pump is then shut off, and the IR analyzer permitted to stabilize while the test head is raised, removing the needles from the culture container. The IR analyzer output is then read, processed by the data system, and stored. Valves V1, V2 and V3 are then opened to purge the head space gas sample from the sample loop. Valves V1, V2 and V3 are closed while the previously energized needle heater assembly NH is then brought into position around the needles, and the pump started to circulate room air through the sampling loop. The pump is then deenergized for a brief period while needle heating continues to aid in the elimination of any biologically active matter present in or on the needles.

Shortly before needle heating is discontinued, the pump is again activated, followed by the opening of V1 and V3. Pressure transducer PT2 is then read and compared to a previously stored limit values to to ensure proper culture gas pressure. Testing continues with a normal reading; an abnormal value above or below the set limits aborts testing and causes warning messages to be issued to check for high or low culture gas pressure, as applicable. Valve V2 is then opened while V1 and V3 remain open and the pump continues to run. Culture gas is permitted to exit from needles N1 and N2. Transducers PT1 and PT2 are again read, and their pressure difference compared to a stored value. A test value lower than the stored constant causes testing to cease and a warning message to be issued to check the pump and associated tubing. The pressure readings of PT1 and PT2 are checked and the values compared to previously stored readings to ensure that the tubing connections are secure and that the needles and filters are free of obstructions. Abnormal values cause the test to be aborted and a warning message to be issued to check tubing connections in the case of low pressure, or to check for obstructions in the case of high pressure recorded by either transducer.

V2 is then opened and the pump shut off, admitting culture gas to both legs of the pneumatic system. PT1 and PT2 are again read, and their readings compared to stored values to ensure that the pressure drop across each needle and its associated filter is within acceptable limits. Abnormal results cause the container test to be discontinued with the issuance of a warning message to check all tubing connections for low pressure sensed be either transducer, or to check needles and filters for obstructions for a high pressure result. All valves are then closed, and the sample changer energized to bring the test head and/or tray into position for the testing of the next container in sequence, whereupon the container test subcycle begins again.

Figure 6:
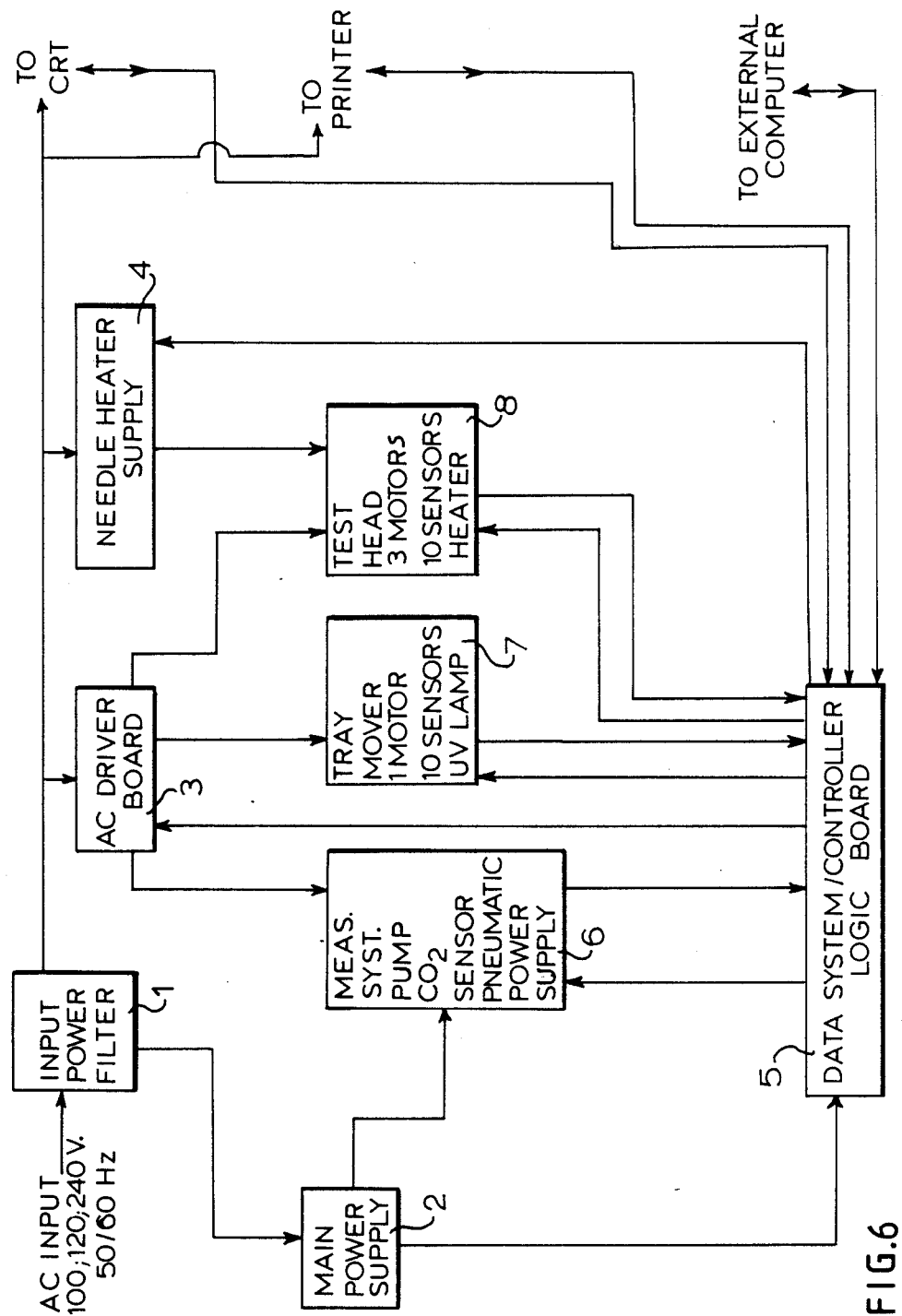
FIG. 6 is a simplified block diagram of the apparatus electronic system.

Control of the measurement system, tray motion, and test head motion and function are accomplished by the data system/controller in conjunction with the associated electronics as shown schematically in FIG. 6. Mains power is conditioned by filter 1 to satisfy domestic and foreign radio frequency interference specifications. Filtered 120VAC power is distributed to the main power supply 2, to the AC driver circuitry 3, and to the needle heater power supply 4. Filtered 120VAC power is also furnished to a convenience outlet to provide power to the external CRT terminal and printer. Logic-level signals from the data system/controller 5 actuate the AC-requiring motors, solenoid valves and the like associated with the measurement system 6, the tray motion assembly 7, and the test head 8 through solid state switches on the AC driver board.

The needle heater power supply is operated in a constant-power mode in order to prevent decay in the efficiency of needle heating as the heating elements increase in resistance due to aging. On/off control of the heater is provided by the controller, which also monitors an error signal generated by the heater power supply to insure proper operation of the heater. The sequencing of solenoid valves and the cycling of the sampling pump are similarly directed by the controller, which also accepts the analog readings from the pressure transducers and IR analyzer as previously described. All analog signals are processed by a multiplexed 10-bit analog-to-digital converter prior to signal processing. Tray motion is similarly controlled through optical sensors which determine tray indexing locations and tray code verification to insure that the aerobic or anaerobic culture gas selected is correct for the tray inserted for test. An ultraviolet lamp used for vial cap irradiation is also processor controlled, and is cycled on only when a tray test is in progress with the appropriate access covers closed to protect the operator from undue UV exposure.

IR analyzer raw data, proportional to infrared transmittance in the region of $CO_2$ absorbance is delivered to the data system/controller in analog form, digitized, and then linearized to reflect carbon dioxide concentration by means of a look-up table resident in the system software. The linearized data is then scaled to provide a reasonable range of numerical values for operator perusal within the range of 0 to 200-300 arbitrary units, termed Growth Values (GV). The maximum value of the scaled data depends upon whether aerobic or anaerobic culture gas is in use, and upon the proportion of the IR analzyer dynamic range consumed by the presence of $CO_2$ in the culture gas. Thus a lower maximum growth value is evidenced when testing anaerobic cultures, owing to the increased $CO_2$ concentration present in the anaerobic culture gas.

All operating system software is stored in read-only memory (ROM), while system scratch-pad memory and data storage occupy random-access memory (RAM). Operation of the system is interrupt driven in conjunction with a real-time clock to control sample test protocol timing and testing. Critical data and system memory contents and real-time clock function are maintained for power outages of at least one week in duration by means of nickel-cadmium battery backup. Power fail/restart circuitry is provided to insure an orderly shutdown of the apparatus upon power failure. Critical system and processor constants are stored upon power failure detection, and are used to restart the system when mains power is returned.

All user interaction with the apparatus is by means of the external CRT terminal via menu-driven screen presentations. Individual menu screens are provided for display selection, the setting of operational parameters, the choice of positive vial detection criteria, the logging of a specimen container onto the system, the obtaining of an aerobic/anaerobic vial pair history in terms of historically measured growth values, the reporting of cultures detected as positive since the previous instrument reading, the performance of a manual test of a tray of culture containers and the performance of daily apparatus maintenance.

In order to insure that the apparatus meets operational specifications in clinical application, self-test provisions are also included in the operating software, including automatic self-test routines to check ROM, RAM, the central processor (CPU), power supply voltage levels, and standby battery condition. These routines are executed while the apparatus is idling between container tests. Operational checks of system operation are also performed on the optical sensors, motors, the needle heater power supply/needle heater, and the measurement system. Daily readiness procedures are also provided to be executed as part of the daily user maintenance protocol which perform detailed checks of the controller, the measurement system, the power supplies, the optical sensors and the various motors. The previously mentioned user maintenance procedures provide fault isolation to the subassembly level of the apparatus.

The growth media utilized in conjunction with the apparatus previously described for the practice of the disclosed method are formulated to characteristics suitable for the growth and detection of aerobic, facultative, and anaerobic microorganisms. It is well understood that oxygen must be provided for the cultivation of strictly aerobic microorganisms, and must be completely minimized, should the cultivation of strict anaerobes be desired. If photoresponsive or phototoxic microorganisms are of interest, light should be provided or excluded accordingly.

Typical culture media generally contain water, a carbon source and a nitrogen source. The carbon source may be a carbohydrate, amino acid, mono- or dicarboxylic acid or salt thereof, polyhydroxy alcohol, hydroxy acid, carbon dioxide/bicarbonate, or other metabolizable carbon or carbon dioxide compound. Some microorganisms assimilate carbon dioxide during growth. Some of these microorganisms require relatively high concentrations of carbon dioxide in the medium due to low affinity of the microorganism for carbon dioxide. Usually the carbon source will comprise at least one sugar such as glucose, sucrose, fructose, xylose, maltose, lactose, etc. Amino acids such as lysine, glycine, alanine, tyrosine, threonine, histidine, leucine, etc. also frequently comprise part of the culture medium carbon source. The nitrogen source may be nitrate, nitrite, ammonia, urea or any other assimilable organic or inorganic nitrogen source. An amino acid or mixture thereof might serve as both a carbon and a nitrogen source. Sufficient nitrogen should be present to facilitate cell growth and replication.

A variety of calcium, potassium and magnesium salts may be employed int he culture medium, including chlorides, sulfates, phosphates and the like. Similarly, phosphate and sulfate ions can be supplied as a variety of salts. As such materials are conventional in microbiological growth media, the selection of specific materials as well as their proportions is within the skill of the art.

The so-called minor elements which are present in trace amounts commonly include manganese, iron, zinc, cobalt and possibly others.

Examples of well known culture media which may be used in the present invention are peptone broth, tryptic soy broth, nutrient broth, thioglycolate broth and brain/heart infusion broth. Tryptic soy broth based media (6B and 7C Media, for aerobic and anaerobic culturing respectively are commercially available from Johnston Laboratories, BBL Microbiology Systems Division of BD, Towson, Md. 21204) have been found to work well.

It is well understood that most biologically active species cannot function in strongly acidic or strongly alkaline media. Similarly, in order for the disclosed method and apparatus to function effectively to detect carbon dioxide produced as a consequence of microorganism metabolism as expressed by an increase in the $CO_2$ content of the culture container head space gas, it is preferable that the pH of the medium be buffered and carefully controlled in order to insure that the proper carbon dioxide/bicarbonate equilibrium is established and maintained in the growth medium prior to inoculation with the suspect samples. Values of pH higher than optimum result in poor release of $CO_2$ from the liquid medium, while media pH values lower than optimum cause excessive $CO_2$ to be present in the head space gas, masking the metabolically produced carbon dioxide. Suitable buffers, such as potassium or ammonium phosphates, sodium citrate, or the like may be employed for purposes of pH adjustment, while various carbonate and bicarbonate salts, as well as gaseous $CO_2$ added to the head space during manufacture of the filled culture vial may be employed to establish the chemical equilibrium most advantageous for detection. Because many species of bacteria, most notably among the anaerobes, require a significant concentration of dissolved carbon dioxide in the culture medium for optimum growth, the aforementioned attention to both pH adjustment and carbon dioxide equilibration act to synergistically enhance both growth and detection.

It should be understood that not all microorganisms metabolize carbohydrate and/or amino acid substrates present in the growth medium to produce carbon dioxide in sufficient quantities for detection by the present method. Such is particularly the case for certain anaerobic microorganisms, most notably among the *Bacteroides*, such as *B. fragilis*. The great majority of such microorganisms do, however, produce considerable quantities of various volatile and nonvolatile organic acids from substrate metabolism.

The present method achieves detection of these microorganisms via detection of the drop in growth medium pH which occurs as a consequence of acid production as indirectly measured by an increase in the container head space $CO_2$ content due to the concurrent shift in the carbonic acid/bicarbonate equilibrium which necessarily accompanies the change in pH. Such indirect detection of metabolism enables detection of growth of a wide range of microorganisms and metabolic patterns through metabolic production of carbon dioxide in the head space gas. Thus, a fundamental contribution of the medium to the method and apparatus of the invention derives from a carefully chosen bicarbonate concentration which both promotes the growth of those organisms with a nutritional requirement for it and permits detection of acid-producing organisms that produce little or no metabolic carbon dioxide. With any suitable buffering system this added bicarbonate raises the concentration of carbon dioxide in the headspace, requiring a corresponding increase in the carbon dioxide concentration in the culture gas. As these concentrations increase, sensitivity of detection of metabolically produced carbon dioxide is reduced.

Two causes contribute to the reduction of sensitivity. At higher concentrations of $CO_2$/bicarbonate in the medium, the difference between the concentration of carbon dioxide in the culture gas and the initial headspace concentration of carbon dioxide tends to have a higher absolute value. A maximum difference of up to twenty percent of carbon dioxide present may exist between the culture gas and the head space gas. For use with these higher concentrations, the carbon dioxide analyzer must have a greater full-scale range and will therefore tend to have errors corresponding to a greater absolute error in carbon dioxide concentration. For the desired spectrum of organisms the optimal concentration of bicarbonate in the growth medium is therefore the minimum concentration which competently supports their growth and yields detection of the acid producers. When these choices are made as set forth for the preferred embodiment of this invention, all pathogenic bacteria ordinarily found in blood cultures can be rapidly detected, yet the time to detection is not greatly increase for those bacteria which could be detected with much less or no bicarbonate in the growth medium.

In general, a medium suitable for providing assimable carbon dioxide as well as providing sufficient carbon dioxide for detection of acid producing microorganisms contains an effective amount of a precursor for carbon dioxide which can produce carbon dioxide by the metabolism of a microorganism present in a sample of materal. The precursor is activated by the generation of acid during metabolism of acid producing microorganisms. The precursor is present at a level of from about 0.5 mM to about 20.0 mM of equivalent bicarbonate per liter of medium preferably from about 1.0 mM to about 10.0 mM of equivalent bicarbonate per liter of medium. Suitable precursors include sodium bicarbonate, dissolved carbon dioxide, sodium carbonate, and other bicarbonate salts.

At the outset of the process, the growth medium is inoculated with a sample of material to be tested while the pH of the medium is maintained between about 6.5 and 8.0 and desirably from about 7.2 to 7.5. The head space gas $CO_2$ concentration is between about 2.0 and 3.0 percent for an aerobic medium, and between about 3.0 and 5.0 percent for an anaerobic medium, subject to the constraints of chemical equilibrium, volume and temperature previously discussed. The amount of sample employed may vary widely, but preferably should be from about 1.0 to 20.0 percent of the growth medium by volume. After a short delay, any viable microorganisms present in the culture medium will grow and replicate, followed by a decrease in growth rate. In addition, the rate of evolution of $CO_2$ will vary depending upon such factors as nutrient composition, pH, temperature, proportion of inoculum, and type of microorganism present.

For effective metabolism for the majority of bacteria, the temperature of the medium with the sample therein is preferably maintained beween about 35° C. and about 37° C. Some microorganisms achieve optimum growth at .temperatures of 20° C. or lower, while others may exhibit optimum growth at 45° C. or higher. This invention may employ any temperature best suited to a given circumstance, provided attention is paid to the concentration of $CO_2$ present in the head space gas of containers held at the desired temperature, and the $CO_2$ concentration of the associated culture gas adjusted to match the head space gas concentration as closely as is practical. Although satisfactory microorganism growth may usually be achieved without agitation of the inoculated culture containers, metabolism is preferably carried out with active shaking, stirring, or the like, effective to insure proper evolution of $CO_2$ from the medium. In one preferred embodiment, external agitation is provided by rotary shaking means to introduce a vortex into the liquid medium.

Turning now more particularly to the practice of the method conducted with the equipment depicted in FIG. 1, the culture containers 1 preferably will have a total capacity of between 30 ml and 150 ml of which 2 ml-100 ml will be occupied by the culture medium and test sample. The volume of blood or urine or other sample may be, for example, 0.1 ml to 10.0 ml. In one preferred embodiment, the culture containers have an overflow volume of approximately 60 ml, and receive 30 ml growth medium and can reseive 3-5 ml sample.

The head space gas thus occupies about 50% of the total container volume. It is preferred that the container headspace comprise between about 30 to about 60 percent of the total container volume. It is somewhat more important that the ratio of the container headspace volume to the volume of the measurement system be maintained as large as possible in light of the foregoing considerations in order to maintain the detection sensitivity of the system.

In order to determine the feasibility of using the apparatus and method herein disclosed to detect the presence of biological activity in simulated blood cultures through analysis of the culture container head space gas, a research prototype instrument was fabricated having the essential features of the apparatus shown in FIG. 1. The pneumatic system employed was essentially equivalent to that described in FIG. 12. A commercially available IR analyzer (Model AR500R Infrared Gas Analyzer, Anarad, Inc., Santa Barbara, Calif. 93105) was employed for $CO_2$ detection, while container testing was accomplished by means of a modified commercially available Model 225 BACTEC instrument. (Johnston Laboratories) The system was controlled by a Cromemco System Three microcomputer (Cromemco, Inc., Mountain View, Calif. 94040). Instrument function and test sequencing were essentially equivalent to previous descriptions given herein.

In order to simulate the low inoculum levels found in clinical blood cultures, and still achieve statistically significant results, the inocula in the simulated blood culturing experiments were prepared at approximately 100 colony forming units (CFU) per container. Organisms for testing were taken from overnight cultures from either agar or broth media. For standardization purposes, several colonies from an agar plate were suspended in 5.0 ml of thioglycollate broth for anaerobes, or tryptic soy broth for aerobes (both from BBL Microbiology Systems, Cockeysville, Md. 21030) in a 16×125 mm screw cap tube, and turbidity adjusted to between 57 and 63 percent transmittance in a Spectronic 88 spectrophotometer (Bausch and Lomb, Rochester, N. Y. 14625) set to 600 nm wavelength. Alternatively, approximately 0.7 ml of turbid broth from a BACTEC vial (Johnston Laboratories) was dispensed into 5.0 ml of broth and turbidity adjusted as above. The standardized broth was three times diluted 1:100 in like broth, and 0.5 ml of the final dilution (approximately 100 CFU) was added to each vial to be tested on the breadboard instrument. Inoculum levels were verified by plate count.

Blood for kinetic growth studies was obtained from Community Blood and Plasma Service (Baltimore, Md. 21231). This blood, sometimes referred to herein as "banked blood", was drawn on order into specially prepared bags containing Sodium Polyanethol Sulfonate (SPS) as anticoagulant in a final concentration of 0.05%. Kinetic studies with *Neisseria meningitidis* were performed with fresh blood, due to potential inhibition of *N. meningitidis* growth by SPS. Growth studies of other fastidious microorganisms were likewise performed using fresh whole blood.

All growth media used in the following examples were from Johnston Laboratories. All anaerobic microorganisms were grown in 7C BACTEC anaerobic medium, flushed but not shaken during testing with anaerobic culture gas. This gas consisted of 2% carbon dioxide, 5% hydrogen, and the balance nitrogen. Aerobic microorganisms were grown in 6BM medium (6B medium with stirring magnets added) and were magnetically stirred on the prototype instrument. Aerobic culture gas consisted of 2.5% carbon dioxide, with the balance air. Incubation temperature for all experiments was controlled between 35° C. and 37° C.

EXAMPLE I

Five slow growing, fastidious microorganisms were tested in blood-supplemented media. Containers were inoculated for each microorganism/broth combination, with each vial containing fresh whole blood from a different individual. Inocula ranged from 8 to 150 CFU/container. Control containers were prepared using fresh whole blood less the microorganism inoculum. Control container results were summed to derive mean and standard deviation data. Containers were tested following inoculation and once per day thereafter. Detection thresholds were chosen to be 19 GV for aerobic cultures and 34 GV for anaerobic cultures based upon experiments to determine worst-case blood metabolism backgrounds.

FIG. 7 presents Growth Values determined as a function of test time for the microorganism *Neisseria meningitidis*. Detection via $CO_2$ evolution is noted to occur on day two of the test. Test and control data remain well separated on the basis of +/−2SD for the remainder of the test. Similar results for *Streptococcus pneumoniae* are shown in FIG. 8. Ample detection is achieved after 24 hours incubation. *Haemophilus influenzae* results are depicted in FIG. 9. Although the microorganism is a weak producer of carbon dioxide, detection is achieved on the second day of testing. Growth results for *Streptococcus pneumoniae* are presented in FIG. 10. A relatively weak, peaked response is observed, but the microorganism clearly achieves detection on the second test day.

Fastidious anaerobic microorganisms were similarly tested. Results obtained with *Bacteroides fragilis* are shown in FIG. 11. Detection is accomplished on the second day of the test. *Bacteriodes vulgatus* detection results exhibit considerable scatter, but detection is achieved by day 5 for all samples tested, as depicted in FIG. 12.

EXAMPLE 2

Kinetic growth investigations were carried out for a set of clinically significant microorganisms, running paired container sets on the prototype IR instrument and on a similar, unmodified BACTEC Model 225 radiometric instrument. Experimental parameters for the kinetic studies are listed in Table 1. Banked blood with 0.05% SPS was used for all microorganism tests except *Neisseria meningitidis*, where freshly drawn blood was used. Data points shown in the following figures are the mean values obtained from multiple test runs plotted as a function of incubation time at 37° C. The arrows indicate the positive detection thresholds for the various experiments. Data for the uninoculated, blood supplemented broth are also shown as mean values of multiple runs, with tests taken at the same time intervals as for the blood supplemented media inoculated with the microorganism. Containers were tested every two hours for rapidly growing microorganisms, and every five hours for slowly growing microorganisms.

TABLE I
INFRARED DETECTION FEASIBILITY STUDY EXPERIMENTAL PARAMETERS FOR KINETIC GROWTH STUDIES

| Parameter | Aerobes | Anaerobes |
|---|---|---|
| Growth Medium | 6 BM (magnetic stirring) | 7 C |
| Culture Gas | 2.5% $CO_2$, Bal. air | 2% $CO_2$, 5% Hc, Bal. N |
| Test Interval | Rapid Growers: 2 h  Fastidious: 3 h | Rapid Growers: 2 h  Slow Growers: 5 h |
| Length of Test | Rapid Growers: 18–14 24 h  Fastidious: 36–45 h | Rapid Growers: 18 h  Slow Growers: 70 h |
| Positive Det'n Threshold, IR | 19 | 34 |
| Postive Det'n Threshold, BACTEC | 20 | 20 |
| | All Studies | |
| Blood | 5.0 ml Banked Blood with 0.05% SPS. | |
| Incubation Temperature | 35–37° C. | |
| Approximate Inoculum | 50–100 CFU/vial, standardized in spectrophotometer; actual numbers determined by plate count. | |

Kinetic data recorded comparing IR detection with radiometric detection for the microorganism *Escherichia coli* is presented graphically in FIG. 13. Time to-detection is essentially equivalent by both methods. Similar results are shown in FIG. 14 for *Klebsiella pneumoniae*. Once again, detection times of the IR method and the conventional radiometric method are shown to be essentially equivalent. The flat-topped response demonstrated for the radiometric BACTEC data represents a full-scale reading on the instrument. *Pseudomonas aeruginosa* is observed to detect somewhat slower by the method herein disclosed, providing both a stronger and a more rapid response with the radiometric method, as shown in FIG. 15. The flat-topped response noted for the radiometric data reflects a full-scale reading of the instrument. Responses observed for *Staphylococcus aureus* are presented in FIG. 16. Detection is shown to be essentially equivalent between systems, but with a stronger response noted for IR detection. Similar behavior is noted for *Staphylococcus epidermidis* as shown in FIG. 17. IR detection in this case provides earlier detection and a more positive response than does the radiometric system. The microorganism *Streptococcus faecalis* was similarly studied, producing the results presented in FIG. 18. IR detection precedes and exceeds radiometric detection for the microorganism. Comparative data for *Streptococcus pneumoniae* is shown in FIG. 19. The detection advantage offered by the disclosed infrared methodology is clearly evidenced. *Haemophilus influenzae* produced responses shown in FIG. 20 when studied. The microorganism was detected above threshold by the radiometric method with slightly better response and more rapid detection than was observed using the infrared system. The yeast *Candida albicans* gave slightly more rapid detection when studied radiometrically, achieving a full-scale response. Detection of the microorganism was essentially equivalent by both systems, as shown in FIG. 21. *Neisseria meningitidis* produced the responses noted in FIG. 22 when comparatively studied. Although detected adequately by both systems, BACTEC methodology provided somewhat earlier and more positive detection.

Organisms cultured anaerobically were also studied for detection kinetics. The microorganism *Clostridium novyii* detected equally well in either system as shown in FIG. 23. Similar results were obtained with *Clostridium perfringens*, as depicted in FIG. 24. Some detection time advantage is gained through IR detection. *Bacteroides fragilis* produced the responses shown in FIG. 25. More rapid detection and response magnitude advantage is noted with BACTEC detection. Such was also the case for *Bacteroides vulgatus*, as presented in FIG. 26.

Results of the kinetic studies are presented in Table 2. On the basis of the matched vial pair kinetic investigations, infrared detection is shown to provide essentially equivalent detection of the selected potentially pathogenic microorganisms studied. Further analysis of the kinetic data on the basis of individual container results for each microorganism, rather than on the average result, proved detection times obtained with the disclosed infrared methodology to be equal to or better than those obtained with the conventional radiometric system in 72% of the tests. Approximately 93% of the tests detected within one test interval of BACTEC or better. Test intervals varied from two hours between tests for rapidly growing microorganisms to five hours for slow growers. The kinetic data is expressed in terms of detection test intervals in FIG. 27.

TABLE 2
COMPARISON OF INFRARED VS. BACTEC DETECTION FOR VARIOUS ORGANISMS - MATCHED VIAL PAIRS

| Organism | # Runs | Inoc. Rng. CFU/vial | Mean Time to Determination Hours[2] IR | Radiometric | Diff.[1] |
|---|---|---|---|---|---|
| 5.0 ml. Banked Blood - 0.5% SPS | | | | | |
| Aerobic Organisms - 6 BM Medium | | | | | |
| E. coli | 8 (2hr) | 62–71 | 10 | 10 | 0 |
| K. pneumoniae | 8 | 62–74 | 10 | 10 | 0 |
| P. aeruginosa | 14 | 53–67 | 15 | 14 | −1 |
| S. aureus | 15 | 4–169 | 12 | 13 | +1 |
| S. epidermidis | 4 | 1–57 | 16 | 18 | +2 |
| S. faecalis | 8 | 75–87 | 12 | 12 | +1 |
| S. pneumoniae | 10 (3 hr) | 18–58 | 18 | 20 | +2 |
| H. influenzae | 10 approx. | 250 | 20 | 17 | −3 |
| C. albicans | 11 | 4–19 | 31 | 33 | +2 |
| N. meningitidis | 8 | 82 | 19 | 19 | 0 |
| Anaerobic Organisms - 7 C Medium | | | | | |
| C. perfringens | 9 (2 hr) | 25 | 10 | 12 | +2 |
| C. novyii | 8 | 21 | 10 | 10 | 0 |
| B. fragilis | 9 (5 hr) | 90 | 29 | 25 | −4 |

TABLE 2-continued

COMPARISON OF INFRARED VS.
BACTEC DETECTION FOR VARIOUS
ORGANISMS - MATCHED VIAL PAIRS

| Organism | # Runs | Inoc. Rng. CFU/vial | Mean Time to Determination Hours[2] | | |
|---|---|---|---|---|---|
| | | | IR | Radiometric | Diff.[1] |
| B. vulgatus | 15 (3 hr) | 100 | 33 | 28 | −5 |

[1]Positive value = IR favored
Negative value = BACTEC favored
[2]Detection Thresholds:
IR, Aerobic = 19
IR, Anaerobic = 34
Radiometric = 20 (both)

EXAMPLE 3

In order to demonstrate the detection sensitivity advantage gained by matching the carbon dioxide concentration of the apparatus culture gas to the concentration of $CO_2$ present in the headspace gas of sterile, uninoculated containers maintained at the desired incubation temperature, a series of experiments were conducted with the microorganism *Bacteroides fragilis* in 7C medium (Johnston Laboratories). Control and test containers were prepared containing 5.0 ml banked blood. Test containers also received approximately 100 CFU of the test microorganism, prepared, diluted and standardized by plate count as in the previous examples. Apparatus culture gases were used having carbon dioxide concentrations of 0%, 2%, 5% and 10%, and having 5% hydrogen present, with the balance nitrogen. Six vial sets, each with a sample and control container, were tested anaerobically on the IR prototype assembly with 35° C. incubation for the 48-hour duration of each experiment for each of the culture gas mixtures tested.

Results obtained with the culture gas containing no carbon dioxide are shown in FIG. 28. Because readings are recorded as the difference between the $CO_2$ concentration in the container headspace gas and the like concentration present in the culture gas, a positive offset is observed for all readings, necessarily adding to the detection threshold and reducing test sensitivity. When the culture gas $CO_2$ concentration is matched to the headspace gas concentration, baseline control values are no longer elevated, and optimum detection is achieved, as presented in FIG. 29. Results obtained with the 5% $CO_2$ mixture are given in FIG. 30. The large negative offset present initially would preclude the detection of rapidly growing microorganisms. Additionally, approximately 15 hours of incubation and associated repeated testing are required in order for the headspace gas $CO_2$ concentration to achieve equilibrium with the culture gas $CO_2$ concentration. The decrease in the growth value difference achieved between the sample and control containers is clearly observed. FIG. 31 depicts results obtained when the culture gas contains 10% carbon dioxide. The initial negative offset is now greatly increased, and detection sensitivity greatly decreased. In addition, approximately 36 test hours and multiple repeat tests are required in order for the headspace $CO_2$ concentration to reach equilibrium with the culture gas.

For proper functioning of the method herein disclosed, it is preferred that the carbon dioxide concentration of the apparatus culture gas be matched as closely as possible to the headspace gas $CO_2$ content of sterile, uninoculated containers to be used in conjunction with the apparatus. This optimum situation provides optimum detection, and minimizes the time required for the culture container headspace gas to reach equilibrium with the apparatus culture gas. Baseline readings remain stable throughout the incubation interval, permitting a detection threshold to be chosen which is time-independent.

EXAMPLE 4

It is well known that some clinically significant microorganisms, most notably among the anaerobes, produce little carbon dioxide as a consequence of substrate metabolism. The majority of these microorganisms do, however, produce considerable quantities of volatile and non-volatile organic acids which are expressed into the medium, tending to lower medium pH. Experiments were thus conducted to determine if the carbon dioxide/bicarbonate chemical equilibrium could be exploited to provide detection of these microorganisms via carbon dioxide released from the growth medium as the chemical equilibrium is shifted due to a lowered medium pH. Indirect liberation of $CO_2$ was first tested in 7C medium with 16.6 mM sodium bicarbonate added. Test vials containing medium plus bicarbonate, and a control vials containing only medium were both subjected to 0.1 ml incremental additions of 0.5M HCl. One vial pair received 0.1 ml acid, the next 0.2 ml, and so forth. Similar vial pairs were prepared for pH measurement. Vial pairs were read on the breadboard instrument, and the liberated $CO_2$ plotted as a function of acid addition as shown in FIG. 32. Detection of the chemically released carbon dioxide is clearly shown through comparison of the test and control vial Growth Value readings. The increase in initial $CO_2$ head space concentration is far outweighed by the response evidenced as the pH is lowered.

The indirect detection system was then tested with a strain of the microorganism *Bacteroides fragilis* known not to produce significant amounts of carbon dioxide as a consequence of metabolism. 7C Medium (Johnston Laboratories) was supplemented with 16.6 mM bicarbonate. Similar control containers not containing bicarbonate were also prepared. 5.0 ml banked blood as previously described was added to each vial; test vials were inoculated with approximately 100 CFU of the microorganism. Results of the test are presented in FIG. 33. Greatly enhanced detection of the microorganism is noted with the bicarbonate-enriched medium. Although blood background readings are elevated somewhat, the benefit of the additional carbon dioxide availability is readily apparent.

What is claimed is:

1. A method for detecting the presence of microorganisms in a sample of material to be analyzed comprising the steps of:
    (a) introducing a test sample into a sterile vial having culture medium and head space gas wherein the culture medium has a carbon source and the head space gas has a known initial $CO_2$ concentration;
    (b) incubating the vial at conditions conducive to metabolism of microorganisms;
    (c) introducing, into a test head for determining carbon dioxide content of gas therein, a culture gas having a $CO_2$ concentration substantially equal to the known initial $CO_2$ concentration of the head space gas;
    (d) determining the $CO_2$ concentration level of the culture gas with the test head, the test head having sensing and motive components for use in sampling the head space gas in the vial;

(e) establishing a fluid communication path between the head space and the test head;

(f) mixing the culture gas in the test head with the head space gas;

(g) measuring in the test head the concentration of $CO_2$ in the mixture of culture gas and the head space gas; and (h) comparing the measured $CO_2$ concentration of the mixture with the $CO_2$ concentration of the culture gas determined in step (d) to detect the presence of microorganisms.

2. The method of claim 1, further characterized by the level of $CO_2$ concentration of a mixture of the culture gas with the test head space gas before said measuring step being within the range of between about 1 and 10 percent.

3. The method of claim 2, further characterized by said level of $CO_2$ concentration of the mixture being within the range of between about 2 and 5 percent.

4. The method of claim 1, wherein the sensing components of the test head have a measuring cell and said step of establishing the fluid communication path enables the measuring cell to measure the $CO_2$ concentration in the mixture.

5. The method of claim 4, further characterized by flushing the fluid communication path with the culture gas before step (d).

6. The method of claim 5, further characterized by providing the culture gas with a level of $CO_2$ concentration within the range of between about 1 and 10 percent.

7. The method of claim 1, further characterized by using whole blood as the sample to be tested.

8. The method of claim 1, further characterized by analyzing a plurality of culture vials in sequence.

* * * * *